United States Patent [19]

Hecker et al.

[11] Patent Number: 5,545,624
[45] Date of Patent: Aug. 13, 1996

[54] DERIVATIVES OF 16-MEMBERED RING ANTIBIOTIC MACROLIDES

[75] Inventors: Scott J. Hecker, Palo Alto, Calif.; Martin R. Jefson, Stonington; James W. McFarland, Lyme, both of Conn.

[73] Assignee: Pfizer Inc., New York, N.Y.

[21] Appl. No.: 362,496

[22] PCT Filed: Jun. 7, 1993

[86] PCT No.: PCT/US93/05210

§ 371 Date: Jan. 11, 1995

§ 102(e) Date: Jan. 11, 1995

[87] PCT Pub. No.: WO94/02496

PCT Pub. Date: Feb. 3, 1994

Related U.S. Application Data

[63] Continuation-in-part of Ser. No. 996,243, Dec. 23, 1992, abandoned, which is a continuation-in-part of Ser. No. 914,242, Jul. 15, 1992, abandoned.

[51] Int. Cl.⁶ .......................... A61K 31/70; C07M 17/08
[52] U.S. Cl. .......................................................... 514/30.000
[58] Field of Search ............................... 514/30; 536/7.1, 536/7.2

[56] References Cited

U.S. PATENT DOCUMENTS

| | | | |
|---|---|---|---|
| 3,975,372 | 8/1976 | Ganguly et al. | 536/17 |
| 4,468,511 | 8/1984 | Kirst et al. | 536/7.1 |
| 4,820,694 | 4/1989 | Debono et al. | 514/30 |
| 4,920,103 | 4/1990 | Kirst et al. | 514/30 |
| 4,921,947 | 5/1990 | Tao et al. | 536/7.1 |
| 5,032,581 | 7/1991 | Lukacs et al. | 514/30 |

FOREIGN PATENT DOCUMENTS

| | | |
|---|---|---|
| 104028 | 3/1984 | European Pat. Off. |
| 103465 | 3/1984 | European Pat. Off. |
| 240264 | 10/1987 | European Pat. Off. |
| 262903 | 4/1988 | European Pat. Off. |
| 59-181299 | 10/1984 | Japan. |
| 59-225199 | 12/1984 | Japan. |
| 2135670 | 9/1984 | United Kingdom. |

OTHER PUBLICATIONS

Chemical Abstracts, vol. 102, 1985, Abstract No. 185436n.
Kirst et al., Journal of Antibiotics, vol. XLII, No. 11, pp. 1673–1683, 1989.
Kirst et al., J. Med. Chem., 1988, 31, pp. 1631–1641.
Debono et al., Journal of Antibiotics, vol. XLII, No. 8, pp. 1253–1267, 1989.
Matsubara et al., Journal of Antibiotics, vol. XXXVI, No. 12, pp. 1713–1721, 1983.
Kirst et al., Journal of Antibiotics, vol. XXXV, No. 12, pp. 1675–1682, 1982.
Koshiyama et al., Journal of Antibiotics, vol. XXII, No. 2, pp. 61–64, 1968.

*Primary Examiner*—Elli Peselev
*Attorney, Agent, or Firm*—P. C. Richardson; Gregg C. Benson; John D. Conway

[57] ABSTRACT

The present invention relates to derivatives of 16-membered ring macrolide antibiotics rosaramicin, repromicin, 5-mycaminosyltylonide, desmycosin, lactenocin, O-demethyllactenocin, cirramycin A1, and 23-deoxymycaminosyltylonide, which are useful against bacterial and mycoplasmic pathogens in animals. Also claimed are a pharmaceutical composition of such derivatives and their use in treating bacterial and mycoplasmic infections in animals.

30 Claims, No Drawings

DERIVATIVES OF 16-MEMBERED RING ANTIBIOTIC MACROLIDES

CROSS REFERENCE TO RELATED APPLICATIONS

This application is the national stage of International Application No. PCT/US93/05210, filed Jun. 7, 1993, designating, inter alia, the United States which is a continuation-in-part of U.S. application Ser. No. 07/996,243, filed Dec. 23, 1992, now abandoned which is a continuation-in-part of U.S. application Ser. No. 07/914,242, filed Jul. 15, 1992, now abandoned.

TECHNICAL FIELD

This invention is concerned with new antibiotics. In particular, this invention relates to compounds which are derivatives of the macrolide antibiotics rosaramicin, repromicin, 5-mycaminosyltylonolide, desmycosin, lactenocin, O-demethyllactenocin, cirramycin $A_1$, and 23-deoxymycaminosyltylonolide; to the pharmaceutically-acceptable acid addition salts of such derivatives; to a method of using such derivatives in the treatment of illnesses in animals caused by bacterial and mycoplasmic pathogens; and to pharmaceutical compositions useful therefor. The term "animals" includes mammals, fish and birds.

There are numerous agents known to combat bacterial infectious diseases in animals, but for many specific diseases the current agents of choice leave much to be desired. In some instances the agents may not persist long enough in the host and, therefore, require frequent dosing to maintain therapeutically effective blood and/or tissue levels. For meat producing animals (cattle, poultry, sheep and swine) this will require considerable labor intensive animal handling which is costly to the producer. In other cases, the agent may be poorly tolerated or even toxic to the host at therapeutically effective doses. Agents with increased potency, a longer half-life, an increased therapeutic index and a broader spectrum of antibacterial activity as well as agents with greater oral absorption would improve the scope of animal diseases that could be more effectively treated. Thus, the need for new antibacterial and anti-mycoplasmic agents with improved properties endures.

Diseases of particular concern are: bovine respiratory disease, the principal causative bacterial pathogens of which are *Pasteurella haemolytica, P. multocida* and *Haemophilus somnus;* pasteurellosis in swine, goats, sheep and poultry (*P. multocida*); swine pleuropneumonia (*Actinobacillus pleuropneumoniae*); swine streptococcus infections (*Streptococcus suis*); and for all of the above mentioned hosts, infections by *Mycoplasma spp.*

BACKGROUND ART

Derivatives of tylosin and its related macrolides have been shown to be effective against infections in poultry, cattle and pigs caused by certain gram-positive and gram-negative bacteria: Kirst et al., U.S. Pat. No. 4,920,103; Tao et al., U.S. Pat. No. 4,921,947; Kirst et al., U.K. Patent Application GB 2135670A.

DISCLOSURE OF THE INVENTION

This invention is concerned with new antibiotics which are derivatives of the macrolides repromicin, rosaramicin, 5-mycaminosyltylonolide, desmycosin, lactenocin, O-demethyllactenocin, cirramycin $A_1$, and 23-deoxymycaminosyl-tylonolide and to the acid addition salts of such derivatives. These new antibiotics have enhanced potency against bacterial pathogens over the parent compounds and are active against mycoplasmic pathogens.

The compounds of the present invention and their pharmaceutically-acceptable salts are of the formula I or II

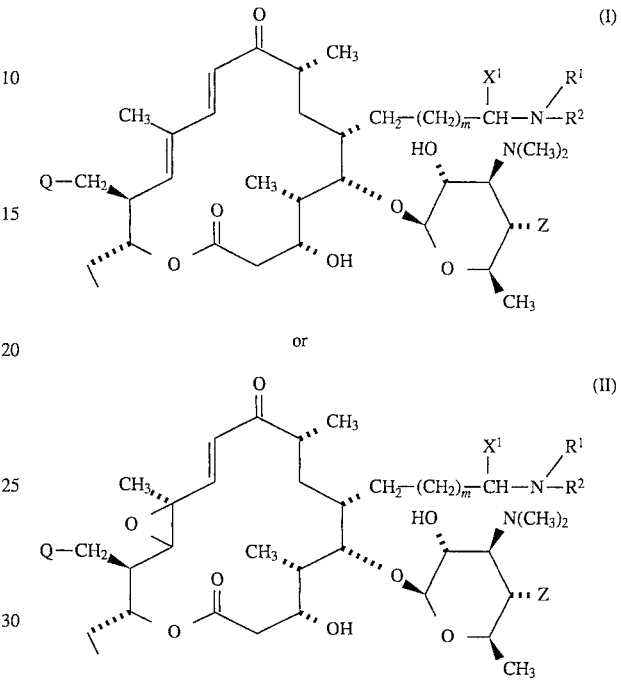

and the pharmaceutically acceptable salts thereof
wherein m is 0 or 1;
$X^1$ is H or CN;
Z is H or OH;
Q is selected from the group consisting of H, OH, fluoro, chloro, bromo, iodo, $OX^2$, $SX^2$,

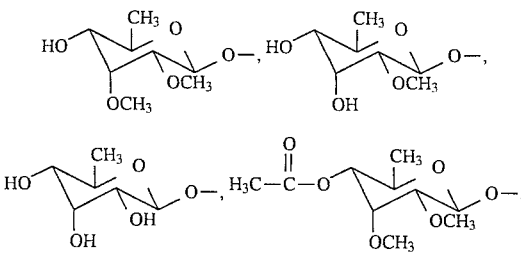

azetidin-1-yl, pyrrolidin-1-yl, piperidin-1-yl, 3,3-dimethylpiperidin-1-yl, hexahydroazepin-1-yl, octahydroazocin-1-yl, octahydroindol-1-yl, 1,3,3a,4,7,7a-hexahydroisoindol-2-yl, decahydroquinol-1-yl, decahydroisoquinol-2-yl, 1,2,3,4-tetrahydroisoquinol-2-yl, 1,2,3,6-tetrahydropyridin-1-yl, 4-alkylpiperazin-1-yl having 1 to 4 carbons in the alkyl portion, morpholino 2,6-dimethylmorpholin-4-yl, thiomorpholino and

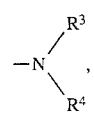

where $R^3$ and $R^4$ are independently selected from the group consisting of H, alkyl having 1 to 4 carbons, hydroxyalkyl having 2 to 4 carbons, cycloalkyl having 3 to 8 carbons, alkenyl having 3 or 4 carbons, alkoxyalkyl having 1 to 4 carbons in the alkoxy portion and 2 to 4 carbons in the alkyl portion and alkoxyalkoxyalkyl having 1 to 4 carbons in each of the alkoxy portions and 2 to 4 carbons in the alkyl portion; and $X^2$ is selected from the group consisting of optionally substituted alkyl having 1 to 4 carbons, optionally substituted cycloalkyl having 4 to 8 carbon atoms, and an optionally substituted aryl, aralkyl or heteroaryl group selected from the group consisting of phenyl, benzyl, pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl;

where the optionally substituted alkyl and optionally substituted cycloalkyl can be substituted with 1 or 2 substituents independently selected from the group consisting of hydroxy, amino, N-alkylamino having 1 to 4 carbons, N,N-dialkylamino having a total of 2 to 6 carbons and alkoxy having 1 to 4 carbons; and where the optionally substituted aryl, aralkyl and heteroaryl groups are optionally substituted with 1 or 2 substituents independently selected from the group consisting of alkyl having 1 to 4 carbons, fluoro, chloro, bromo, acetyl, amino, nitro, cyano, trifluoromethyl, N-alkylamino having 1 to 4 carbons, N,N-dialkylamino having a total of 2 to 6 carbons, carboxyl, carboalkoxy having 1 to 4 carbons, carboxamido, sulfonamido, hydroxyalkyl having 1 to 4 carbons, aminoalkyl having 1 to 4 carbons, N-alkylaminoalkyl having 1 to 4 carbons in each of the alkyl portions, and N,N-dialkylaminoalkyl having a total of 2 to 6 carbons in the dialkylamino portion and 1 to 4 carbons in the alkyl portion;

$R^1$ is selected from the group consisting of H, alkyl having 1 to 4 carbons, aminoalkyl having 2 to 4 carbons, hydroxyalkyl having 2 to 4 carbons, N-alkylaminoalkyl having 1 to 4 carbons in the alkylamino portion and 2 to 4 carbons in the alkyl portion, benzyl, alkoxyalkyl having 2 to 4 carbons in the alkyl portion and 1 to 4 carbons in the alkoxy portion, N,N-dialkylaminoalkyl having a total of 2 to 6 carbons in the dialkylamino portion and 2 to 4 carbons in the alkyl portion, morpholino-$(C_2-C_4)$alkyl, piperidino-$(C_2-C_4)$alkyl, pyrrolidino-$(C_2-C_4)$alkyl, azetidinyl-$(C_2-C_4)$alkyl, and $X^3$;

$R^2$ is selected from the group consisting of optionally substituted alkyl having 1 to 6 carbons,

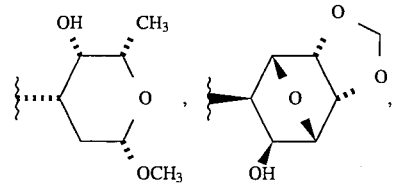

optionally substituted cycloalkyl having 3 to 8 carbons, and

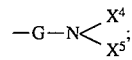

wherein the optionally substituted alkyl is optionally substituted with 1 or 2 substituents independently selected from the group consisting of hydroxy, cyano, amino, N-alkylamino having 1 to 4 carbons, N,N-dialkylamino having a total of 2 to 6 carbons, N-(hydroxyalkyl)amino having 2 to 4 carbons, N,N-bis(hydroxyalkyl)amino wherein each alkyl portion has 2 to 4 carbons, alkoxy having 1 to 4 carbons, alkoxycarbonyl having 1 to 4 carbons in the alkoxy portion, N,N-dialkylaminoalkoxy having a total of 2 to 6 carbons in the dialkylamino portion and 2 to 4 carbons in the alkoxy portion, alkoxyalkoxy having 1 to 4 carbons in each of the alkoxy portions, alkoxyalkoxyalkoxy having 1 to 4 carbons in each of the alkoxy portions,

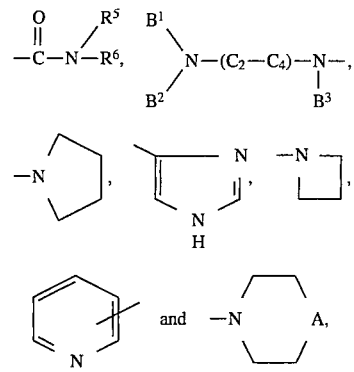

wherein $R^5$ and $R^6$ are independently selected from hydrogen or alkyl having 1 to 4 carbons, or $R^5$ and $R^6$ are taken together with the nitrogen to which they are attached and form a saturated or unsaturated ring having 4 to 6 carbon atoms, morpholino or piperazino;

A is $CH_2$, NH, O, S or N-loweralkyl; and $B^1$, $B^2$, and $B^3$ are each independently selected from the group consisting of hydrogen and $(C_1-C_4)$alkyl;

the optionally substituted cycloalkyl is optionally substituted with 1 to 5 substituents independently selected from the group consisting of hydroxy, fluoro, chloro, alkoxy having 1 to 4 carbons, hydroxyalkyl having 1 to 4 carbons, alkoxyalkyl having 1 to 4 carbons in each of the alkoxy and alkyl portions, amino, N-alkylamino having 1 to 4 carbons, N,N-dialkylamino having a total of 2 to 6 carbons and

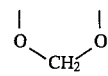

where the oxygen atoms are attached to adjacent carbon atoms of the cycloalkyl;

G is $(C_2-C_4)$alkylene optionally substituted with $(C_1-C_4)$alkyl or hydroxyl;

$X^4$ is selected from the group consisting of hydrogen, methyl and ethyl;

$X^3$ and $X^5$ are independently selected from the group consisting of an optionally substituted hydroxyalkanoyl having 1 to 6 carbons, an amino acyl group, and dipeptidyl group, wherein the amino acyl group and the amino acyl groups of the dipeptidyl group are independently selected from the group consisting of the D- or L-form, when applicable, of alanyl, arginyl, asparagyl, aspartyl acid, cysteinyl, cystyl, glutamyl acid, glutamyl, glycyl, histidyl, hydroxyllysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N-N-diethyl-β-alanyl, N,N-dimethyl-γ-aminobutyryl and sarcosyl; and the optionally substituted hydroxyalkanoyl group is optionally substituted with an optionally substituted phenyl, wherein the optionally substituted phenyl is optionally substituted with 1 to 5 substituents selected from the group consisting of $(C_1-C_4)$alkyl, fluoro, chloro, bromo, iodo, $(C_1-C_4)$alkoxy, nitro, amino, cyano, hydroxy, trifluoromethyl and carboalkoxy having 1 to 4 carbons;

or $X^4$ and $X^5$ are taken together with the nitrogen to which they are attached and form

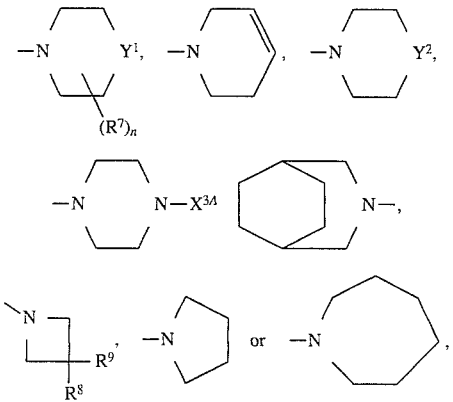

where $Y^1$ is selected from the group consisting of C, CH, $CH_2$, N and NH; $Y^2$ is O or S; n is 0, 1 or 2; $R^7$ is alkyl having 1 to 4 carbons

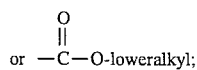

or —C—O-loweralkyl;

$R^8$ is H or alkyl having 1 to 4 carbons; $R^9$ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or $R^8$ and $R^9$ are taken together and form an oxo group; and $X^{3A}$ is independently selected from the same group as $X^3$;

or $R^1$ and $R^2$ are taken together with the nitrogen to which they are attached and form

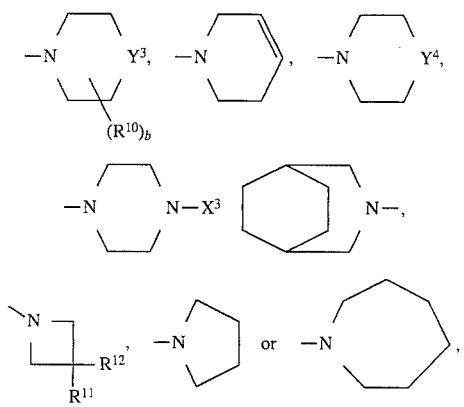

where $Y^3$ is selected from the group consisting of C, CH, $CH_2$, N and NH; $Y^4$ is O or S; b is 0, 1 or 2; $R^{10}$ is alkyl having 1 to 4 carbons

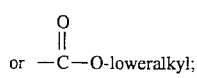

or —C—O-loweralkyl;

$R^{11}$ is H or alkyl having 1 to 4 carbons; $R^{12}$ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or $R^{11}$ and $R^{12}$ are taken together and form an oxo group; and $X^3$ is as defined above;

provided that:

(1) for a compound of formula I when m is 0, $X^1$ is H, Z is H or OH, $R^1$ is H, benzyl, alkyl having 1 to 4 carbons, hydroxyalkyl having 2 to 4 carbons, or alkoxyalkyl having 2 to 4 carbons in the alkyl portion and 1 to 4 carbons in the alkoxy portion, and Q is other than azetidin-1-yl, $R^2$ cannot be unsubstituted alkyl or unsubstituted cycloalkyl and $R^1$ and $R^2$ taken together with the nitrogen to which they are attached cannot form

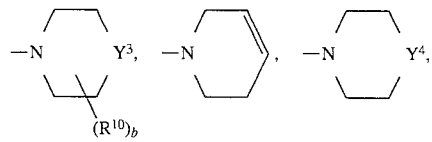

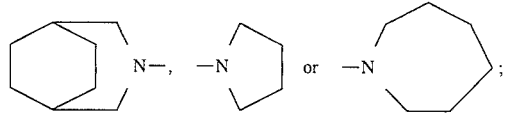

wherein $Y^3$, $R^{10}$, b and $Y^4$ are as defined above;

(2) when $R^2$ is a substituted cycloalkyl, then the hydroxy and amino substituents cannot be attached to the 1-position of said substituted cycloalkyl;

(3) when $R^2$ is a substituted cyclopropyl or substituted cyclobutyl, then

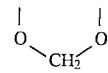

cannot be a substituent; and (4) for a compound of formula I when m is 0, $X^1$ is CN, Z is OH, Q is hydroxy or

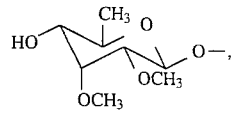

and $R^1$ is H or alkyl having 1 to 4 carbons, $R^2$ cannot be unsubstituted alkyl.

The term "loweralkyl" denotes an alkyl having 1 to 4 carbons. The term "alkyl" is meant to encompass both straight chain and branched alkyls.

Those skilled in the art will recognize that some of the compounds of the present invention possess stereochemical centers. In those cases where stereochemical centers are present it is understood that all of the stereoisomers are within the scope of this application.

As will be readily apparent to one skilled in the art when $X^2$ is an optionally substituted heteroaryl group, the O or S, to which $X^2$ is attached, cannot be attached to the heteroaryl group through a heteroatom of the ring.

The amino acyl groups are derivatives of the corresponding amino acids and are well known in the art. The following D- or L-amino acids, where applicable, are used to derive the amino acyl groups of this invention: alanine, arginine, asparagine, aspartic acid, cysteine, cystine, glutamic acid, glutamine, glycine, histidine, hydroxyllysine, hydroxyproline, isoleucine, leucine, lysine, methionine, phenylalanine, proline, serine, threonine, tryptophane, tyrosine, valine, β-alanine, β-lysine, N,N-dimethylglycine, α,α-dimethylglycine, α-aminobutyric acid, 4-hydroxyphenylglycine, phenylglycine, α,α-diaminobutyric acid, ornithine, homoserine, bicine, N,N-diethyl-β-alanine, N,N-dimethyl-γ-aminobutyric acid, and sarcosine.

The dipeptidyl groups comprise derivatives of any possible combination of two of the amino acids listed hereinabove which have been coupled by conventional peptide synthesis methods well known to those skilled in the art.

The hydroxyalkanoyl groups are derivatives of the corresponding alkanoic acids and are well known in the art. A few examples of such groups, which are listed for illustration purposes and are not intended to limit the scope of the group, are glycolic acid, lactic acid and mandelic acid.

A preferred group of compounds are those having the formula (I) or (II) where m is 0.

Another preferred group of compounds are those having the formula (I) wherein m is 0; Z is H; $R^1$ is selected from the group consisting of H, alkyl having 1 to 4 carbons, hydroxyalkyl having 2 to 4 carbons and alkoxyalkyl having 2 to 4 carbons in the alkyl portion and 1 to 4 carbons in the alkoxy portion; $R^2$ is substituted alkyl having 2 to 5 carbons, wherein the substituents are selected from the group consisting of amino, N-alkylamino having 1 to 4 carbons, and N,N-dialkylamino having a total of 2 to 6 carbons; and Q is selected from the group consisting of hydrogen, homopiperidin-1-yl, piperidin-1-yl, pyrrolidin-1-yl, N,N-diethylamino, N,N-dimethylamino, N,N-dipropylamino,

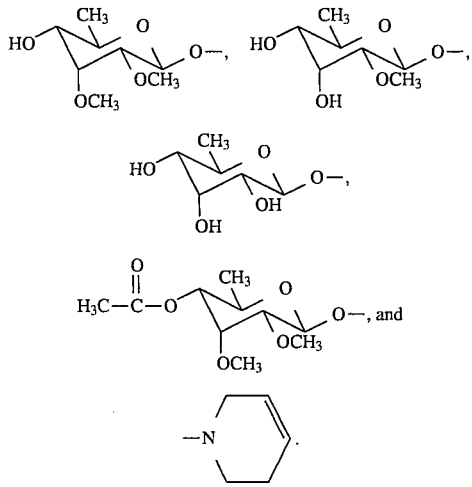

Yet still another group of preferred compounds are those having formula (II) wherein m is 0; Z is H; $R^1$ is selected from the group consisting of H, alkyl having 1 to 4 carbons, and alkoxyalkyl having 2 to 4 carbons in the alkyl portion and 1 to 4 carbons in the alkoxy portion; $R^2$ is selected from the group consisting of H, alkyl having 1 to 4 carbons and substituted alkyl having 2 to 5 carbons, wherein the substituents are selected from the group consisting of amino, N-alkylamino having 1 to 4 carbons, hydroxy, alkoxy having 1 to 4 carbons and N,N-dialkylamino having a total of 2 to 6 carbons; or $R^1$ and $R^2$ are taken together with the nitrogen to which they are attached and form a heterocyclic group selected from the group consisting of azetidinyl, pyrrolidino, piperidino, hexahydroazepinyl, and morpholino; and Q is hydrogen.

Further, another preferred group of compounds are those compounds having the formula (I) wherein m is 0; $R^1$ is $X^3$; $X^1$ is H; $R^2$ is 3-(dimethylamino)propyl; and Q, Z and $X^3$ are as defined above for formula (I). A more preferred group of compounds within the above group of compounds are those wherein $X^3$ is an amino acyl group selected from the group consisting of L-alanyl. D-alanyl, glycyl, L-valyl, N,N-dimethylglycyl, N,N-dimethyl-γ-aminobutyryl, N,N-diethyl-β-alanyl, sarcosyl, α,α-dimethylglycyl and α-aminobutyryl. The two most preferred compounds of this group of more preferred compounds are those wherein Q is H; Z is H and $X^3$ is glycyl, and wherein Q is H; Z is H and $X^3$ is L-alanyl.

Furthermore, another group of preferred compounds are those compounds having the formula (I) wherein m is 0; $R^1$ is hydrogen or methyl; $R^2$ is

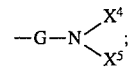

and Q, Z, $X^4$ and $X^5$ are as defined above for formula (I). A more preferred group of compounds within this immediate group of compounds are those wherein G is propylene or 2,2-dimethylpropylene, $X^4$ is hydrogen or methyl and $X^5$ is an amino acyl group selected from the group consisting of L-alanyl, D-alanyl, glycyl, L-valyl, N,N-dimethylglycyl, sarcosyl, α,α-dimethylglycyl and α-aminobutyryl. The two most preferred compounds of this group of more preferred compounds are the compounds wherein Q is H; Z is H; $X^4$ is H; $R^1$ is H; G is 2,2-dimethylpropylene; and $X^5$ is L-alanyl; and wherein Q is H; Z is H; $X^4$ is methyl; $R^1$ is methyl; G is propylene and $X^5$ is glycyl.

The parent macrolides from which the compounds of this invention can be made are generally derivatized at the C-20 position with certain substituted amino groups. These derivatives are formed by reductive amination of the C-20 aldehyde group using reducing agents such as formic acid, sodium borohydride, sodium cyanoborohydride or sodium triacetoxyborohydride. The cyano derivative of the reductive amination products are inherently produced, in the reaction utilizing sodium cyanoborohydride, along with the non-cyano reductive amination product. Scheme I, below, shows a method to obtain the intermediate for compounds of this invention where m is 1. Schemes II and III, below, illustrate the general reductive aminations employed for obtaining the compounds of this invention. In Schemes I to III X is either

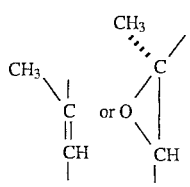

corresponding to general formulas (I) and (II), respectively.

Scheme I

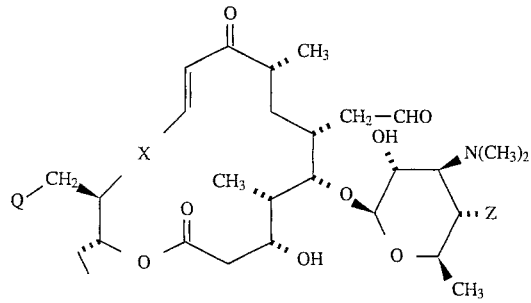

1) Potassium tert-butoxide, CH₃OCH₂P(C₆H₅)₃Cl
2) H₃O⁺

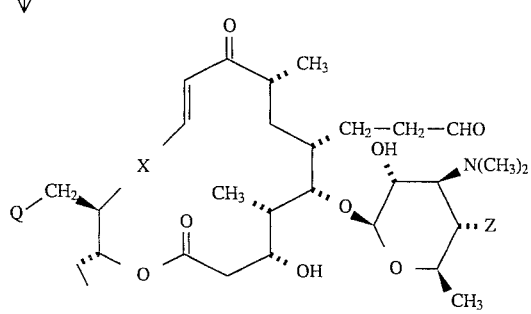

Scheme II

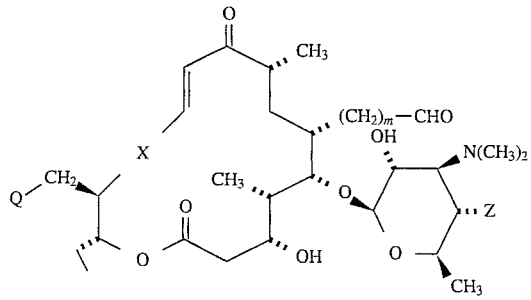

Method A
1) HNR¹R²
2) Formic Acid Δ

Method D
1) HNR¹R²
2) 0° C., Acetic Acid
3) NaBH₃CN

-continued
Scheme II

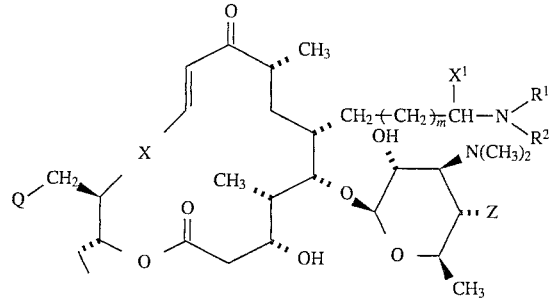

Scheme III

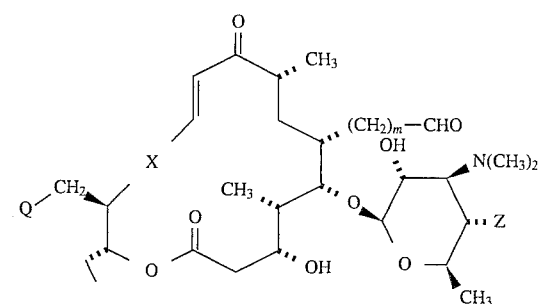

1) H₂NR²
2) NaBH₃CN

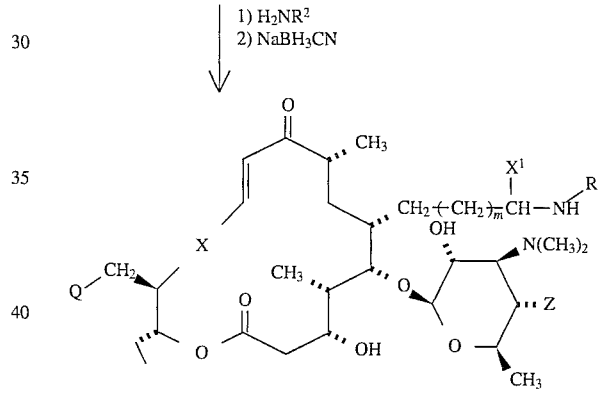

1) Formic Acid, Formaldehyde Reflux

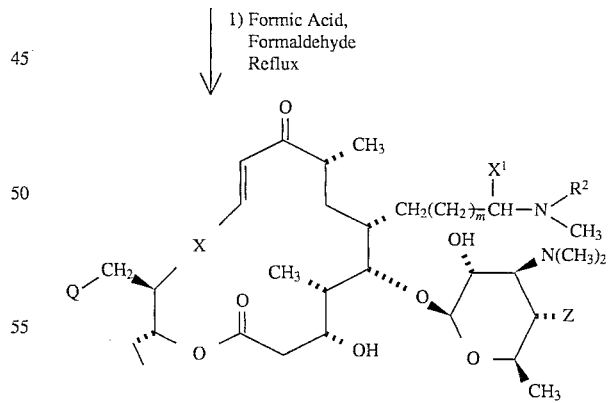

The compounds of the present invention, having the formula I or II, as defined above, are readily and generally prepared by reductive amination reactions of the appropriate macrolide, rosaramicin, repromicin, 5-mycaminosyltylonolide, desmycosin, lactenocin, O-demethyllactenosin, cirramycin $A_1$, or 23-deoxymycaminosyltylonolide, with an amine, optionally followed by conversion to the acid addition salt as detailed below.

Derivatization of the parent macrolide at the C-23 position is carried out according to the method well known to those skilled in the art and as described in J. Antibiotics, 40(6), pp. 823–842, 1987, the contents of which are incorporated herein by reference.

The particular reaction conditions and reagents used to derivatize a compound of formula I or II at the C-20 position are dictated by the kind of amine that is used in the reaction. When secondary amines are used in the reductive amination, the following procedure is utilized. A solution of a macrolide, such as repromicin, is mixed with an excess, usually about 1.5 molar equivalent, of a secondary amine such as azetidine in a reaction inert solvent such as ethyl acetate. The reaction mixture is heated to about 60° C. to 80° C., preferably about 70° C., with stirring. A slight excess of formic acid, usually about 1.1 molar equivalent, is added dropwise to the reaction mixture and the temperature of the reaction mixture is lowered by about 5° C. The reaction is stirred for an additional four to seven hours, but usually for about five hours. The reaction is stopped by cooling to room temperature and the desired C-20 amino derivative of the macrolide is isolated by standard techniques well known to those skilled in the art, such as column chromatography or crystallization.

If the type of amine to be used in the reductive amination is a primary amine, then the following method is employed. A solution of sodium cyanoborohydride and the primary amine is made in a reaction-inert solvent such as methanol. The sodium cyanoborohydride is present at approximately four molar equivalents and the amine is present at about one molar equivalent of the macrolide. A methanol solution of the macrolide is added dropwise to the solution of sodium cyanoborohydride and the primary amine, and the mixture is stirred for about three to six hours, preferably about four hours. The desired C-20 amino derivative of the macrolide is isolated by standard techniques well known to those skilled in the art. The cyano derivative, where $X^1$ is CN, is also produced in the reaction and can be isolated by standard techniques well known to those skilled in the art.

The cyano derivatives can also be synthesized separately by the following method. A solution of zinc iodide and an appropriate macrolide is made in methanol. Trimethylsilylcyanide is added to the methanol solution and is stirred for about 15 minutes then the appropriate amine is added and the solution is heated at about 40° C. for about 2 hours. The desired cyano derivative is isolated by standard methods well known in the art.

A C-20 primary amino derivative of the macrolide, formed by the above method, can be further derivatized by N-methylating the secondary amino group at the C-20 position. This synthesis is carried out by suspending the C-20 secondary amino macrolide derivative in water and then adding formic acid. To the resulting solution, a 38% solution of aqueous formaldehyde is added and the reaction mixture is heated to reflux temperature. The reaction mixture is stirred at reflux for about four to six hours, preferably about five hours. It is then cooled to room temperature and the desired compound is isolated.

When a functionalized amine such as N,N-dimethyl-1,3-propanediamine is used for reductive amination, the following is a method of effecting a reductive amination. A methanol solution of the macrolide is mixed with the appropriate amine and stirred at room temperature for approximately 30 minutes. The reaction mixture is then cooled to about 0° C. and an equimolar amount of glacial acetic acid is added to the mixture and the reaction allowed to stir. After about ten minutes of stirring, a methanol solution of sodium cyanoborohydride is added to the reaction mixture, and the resulting solution is stirred for about one hour at about 0° C. The reaction is stopped by warming to room temperature and concentrating the reaction mixture, and then the desired macrolide derivative is isolated. A preferred method of accomplishing the same type of reaction is as follows. To a stirring solution of the macrolide in methanol is added the appropriate amine and stirred for about 30 minutes. The solution is then cooled to about 0° C. and sodium borohydride is added to it. After stirring for about 2 hours, the solution is concentrated to near dryness and the desired compound is isolated by conventional methods well known in the art.

A secondary amine at the C-20 position can be further functionalized with an amino acyl group according to the following procedure. A dichloromethane solution of a N-protected amino acid or N-protected dipeptide (t-BOC is one of the preferred protecting groups), or an O-protected hydroxyalkanoic acid (acetate is one of the preferred protecting groups), dicyclohexylcarbodiimide and hydroxybenzotriazole (all of which are present in equimolar amounts) is cooled to about 0° C. To the cold solution is added a C-20 secondary amino compound of formula I or II; wherein $R^1$ is hydrogen and $R^2$ is as defined above. The solution is allowed to warm to room temperature and stirring is continued for about 48 to 72 hours. The crude product is isolated by conventional methods such as chromatography. The N-protected amino acyl, N-protected dipeptidyl or O-protected hydroxyalkanoyl derivative is deprotected by conventional methods to yield the desired product.

A compound of formula I or II wherein the C-20 position is an aminoalkylamino can be further derivatized at the terminal amine by an amino acyl group according to the following procedure. To a stirring solution of a compound of formula I or II having an aminoalkylamino group at the C-20 position in dimethylformamide is added a N-protected (t-BOC is preferred protecting group) amino acid hydroxysuccinimide ester, and the mixture is stirred for about 6 hours. The crude product is isolated by conventional methods such as silica gel chromatography. The N-protected amino acyl derivative is deprotected by conventional methods to yield the desired products.

The pharmaceutically acceptable acid addition salts of the C-20 amino macrolide derivatives can be obtained by the following general procedure. For example, the HCl salts can be isolated by dissolving the C-20 amino macrolide derivative in a methanolic HCl solution and then evaporating the volatile components to yield the desired salt. The methanolic HCl solution can be prepared by mixing acetyl chloride with methanol. In addition to the HCl salts, other preferred pharmaceutically acceptable acid addition salts include citrate, phosphate, sulfate, methanesulfonate, palmitate, succinate, lactate, malate, maleate, tartrate, besylate, fumarate and stearate salts. All of such salts are prepared in a method analogous to the method used to form the HCl salt, that is, by adding equivalent amounts of the appropriate acid to the base.

The starting macrolide rosaramicin is produced and isolated according to the method described by Wagman et al. In Journal of Antibiotics, Vol. XXV, No. 11, pp. 641–646, November 1972. Repromicin is synthesized from rosaramicin using the method taught by Ganguly et al. in U.S. Pat.

No. 3,975,372. Desmycosin, lactenocin, O-demethyllactenocin and 23-deoxymycaminosyltylonolide are produced and isolated according to the method described in Journal of Antibiotics, 35(12), pp. 1675–1682, 1982. Cirramycin $A_1$, is produced and isolated according to the method described in Journal of Antibiotics, 22, p. 61, 1969. The contents of the above references are incorporated herein by reference. All other starting materials and reagents required for the synthesis of the compounds of the present invention are readily available commercially or can be prepared according methods known in the literature.

The antibacterial activity of the compounds of the present invention against bacterial pathogens is demonstrated by the compound's ability to inhibit growth of *Pasteurella multocida* and *Pasteurella haemolytica*. The following procedures are typical assays. Assay I is utilized to test for activity against *Pasteurella multocida* and Assay II is utilized to test for activity against *Pasteurella haemolytica*.

ASSAY I

(*P. multocida*)

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 µl of dimethylsulfoxide (DMSO). Dilutions of the test compound are prepared using uninoculated BHI broth. The concentrations of the test compound used range from 200 µg/ml to 0.098 µg/ml by two-fold serial dilutions. The *P. multocida* inoculated BHI is diluted with uninoculated BHI broth to make a $10^4$ cell suspension per 200 µl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

ASSAY II

(*P. haemolytica*)

This assay is based on the agar dilution method using a Steers Replicator. Two to five colonies isolated from an agar plate are inoculated into BHI broth and incubated overnight at 37° C. with shaking (200 rpm). The next morning, 300 µl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 µl of the *P. haemolytica* culture is inoculated onto BHI agar plates containing the various concentrations of the test compound using a Steers Replicator and incubated for 18 hours at 37° C. Initial concentrations of the test compound range from 100–200 µg/ml. The MIC is equal to the concentration of the test compound exhibiting 100% inhibition of growth of *P. haemolytica* as determined by comparison with an uninoculated control.

The in vivo activity of the compounds of formula I or II can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or per os. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded on the form provided. The *P. multocida* model monitoring continues for 96 hours (four days) post challenge. Surviving mice are asphyxiated with carbon dioxide at the end of the study.

The $PD_{50}$ is a calculated dose at which the compound tested protects 50% of a group of mice from mortality due to the bacterial infection which would be lethal in the absence of drug treatment.

To implement the methods of this invention, an effective dose of a compound of formula I or II is administered to a susceptible or infected animal by parenteral (i.v., i.m. or s.c.), oral or topical route. The effective dose will vary with the severity of the disease, and the age, weight and condition of the animal. However, the dose will usually range from about 0.25 to about 150 mg/kg, preferably from about 0.25 to about 25 mg/kg.

A suitable vehicle for administering the dose parenterally is a solution of the compound in steril water, or a solution of the compound in a solvent comprising at least 50% water and a pharmaceutically acceptable cosolvent or cosolvents such as methanol, ethanol, isopropyl alcohol, propylene glycol, glycerol, carbonate esters like diethyl carbonate, dimethyl sulfoxide, N,N-dimethylformamide, N,N-dimethylacetamide, 1-methyl-2-pyrrolidinone, and the like. Suspensions are also suitable vehicles for administering the compounds of this invention. The suspending medium can be, for example, aqueous carboxymethyl cellulose, inert oils such as peanut oil, highly refined mineral oils, aqueous polyvinylpyrrolidone and so forth. Suitable physiologically acceptable adjuvants may be necessary to maintain the compound in suspension. These adjuvants may be chosen from among thickeners such as carboxymethyl cellulose, polyvinylpyrrolidone, gelatin, and the alginates. Surfactants are also useful as suspending agents. These surfactants include: lethicin, alkylphenol polyethylene oxide adducts, naphthalenesulfonates, alkylbenzenesulfonates and polyoxyethylene sorbitan esters. Agents affecting surface tension can also help in making useful suspensions. Such agents include silicone antifoams, sorbitol, and sugars. For intravenous use the total concentration of solutes should be controlled to render the preparation isotonic.

Thus in a further aspect the invention provides pharmaceutical compositions comprising a compound of the formula (I) or (II) or pharmaceutically acceptable salts thereof together with a pharmaceutically acceptable carrier or diluent.

This invention also provides a method of treating a bacterial infection or a mycoplasmic infection in an animal in need thereof which method comprises administering to said animal a bacterial or mycoplasmic treating amount of a compound of the formula (I) or (II) or a pharmaceutically acceptable salt thereof.

The present invention is illustrated by the following examples, but is not limited to the details thereof. High Performance Liquid Chromatography (HPLC) retention times of the products of this invention are determined on a Zorbax RX®, 5 micron C8 column (4.6 mm ID×15 cm length) from Dupont (available from Mac-Mod Analytical Inc., 127 Commons Court, Chadds Ford, Pa. 19317 1-800-441-7508). A 45:55 (vol:vol) mixture of acetonitrile to aqueous 50 millimolar ammonium acetate is used as the eluant. The column temperature is maintained at 40° C. and the flow rate is 1.0 ml per minute. Samples are dissolved in the eluant (2 mg/ml) and are injected (70 μl) into a Hewlett-Packard 1090 high performance liquid chromatography instrument; peaks corresponding to the sample input are detected by ultraviolet spectroscopy at either 254 or 280 nm.

EXAMPLE 1

(Method A)

20-(Azetidin-1-yl)-20-deoxorepromicin dihydrochloride

A solution of repromicin (6.61 g, 11.69 mmol), azetidine (1.00 g, 17.51 mmol) and 225 ml of ethyl acetate was heated to 70° C. with stirring. Formic acid (0.591 g, 12.8 mmol) was added dropwise to the solution, and the temperature was lowered to 65° C. Stirring and heating was continued for five hours. After cooling to room temperature, the reaction mixture was washed twice with 250 ml portions of saturated aqueous sodium bicarbonate and then washed once with 200 ml of saturated aqueous sodium chloride. The combined aqueous washes were extracted with four 100 ml portions of ethyl acetate. The combined organic extracts were dried over anhydrous magnesium sulfate, filtered and then evaporated under reduced pressure to yield 6.56 g of crude product as a yellow foam. This material was taken up in 100 ml of hot diethyl ether; insolubles were filtered and saved. The filtrate was treated with 300 ml of hot hexane, and again the resulting insoluble matter was filtered and saved. The filtrate was concentrated to about 75 ml by boiling off excess solvent. The resulting solution was allowed to cool to room temperature, and then cooled further to 5° C. for several hours. A colorless precipitate of 20-(azetidin-1-yl)-20-deoxorepromicin formed, yield 2.58 g (36%); m/e 607.4 (theory 607); HPLC retention time (RT): 12.91 minutes. The filtrate from the initial product was combined with the insolubles that were saved, and the mixture was then chromatographed on 450 cc of silica gel. Elution with 1:9 methanol/dichloromethane containing 1% ammonium hydroxide afforded 1.88 g (27%) of additional product for a total yield of 63% of the free base. Acetyl chloride (1.15 g, 14.66 mmol) was added dropwise to 75 ml of methanol, and the solution was allowed to stand at room temperature for 75 minutes. To this methanolic HCl solution was added 4.45 g (7.33 mmol) of 20-(azetidin-1-yl)-20-deoxorepromicin. The resulting pale yellow solution was allowed to stand at room temperature for two hours. The volatile components were evaporated and the residue was dried under reduced pressure to give 5.24 g of the title compound.

EXAMPLE 2

(Method B)

20-(3-Azabicyclo[3.2.2]non-3-yl)-20-deoxorosaramicin dihydrochloride

Under a nitrogen atmosphere and with magnetic stirring at room temperature, a solution of sodium cyanoborohydride (0.888 g, 14.1 mmol), 3-azabicyclo[3.2.2]nonane (0.398 g, 3.52 mmol), and 40 ml of methanol was treated dropwise with a solution of rosaramicin (2.05 g, 3.53 mmol) in 20 ml of methanol. The resulting solution was stirred for four hours and then evaporated under reduced pressure. The residue was chromatographed on silica gel using 1:9 methanol/dichloromethane containing 1% ammonium hydroxide as the eluant. Isolation yielded 0.910 g (41%) of the free base of the title compound, m/e, 691.3; HPLC RT: 23.36 minutes. Acetyl chloride (0.24 ml, 0.265 g, 3.38 mmol) was added dropwise to 15 ml of methanol, and the solution was allowed to stand at room temperature for 45 minutes. To this solution of methanolic HCl was added 0.825 g (1.21 mmol) of 20-(3-azabicyclo[3.2.2]non-3-yl)- 20-deoxorosaramicin. The resulting pale yellow solution was allowed to stand at room temperature for two hours. The volatile components were evaporated and the residue was dried under reduced pressure to give 0.786 g of the title compound.

EXAMPLE 3

(Method C)

20-[N-Methyl-N-(3-(morpholino)propyl)amino]-20-deoxorepromicin hydrochloride

20-[3-(Morpholino)propyl]amino-20-deoxorepromicin was prepared from repromicin and 3-(morpholino)propylamine by Method B (omitting the HCl salt formation step). To a suspension of 20-[3-(morpholino)propyl]amino-20-deoxorepromicin (200 mg, 0.290 mmol) in 1.25 ml of water was added 517 mg of formic acid. The resulting solution was treated with 84 μl (1.15 mmol) of 38% aqueous formaldehyde, and then heated under reflux with stirring for five hours. The reaction mixture was allowed to cool to room temperature, and then was stored at 5° C. for overnight. The volatile components were distilled under vacuum and the residue was partitioned between saturated aqueous sodium bicarbonate and diethyl ether. The aqueous layer was extracted with ether. The combined organic layers were dried over anhydrous potassium carbonate, filtered, and evaporated under reduced pressure. Dichloromethane was added to the residue and the volatile components were evaporated under reduced pressure to furnish 170 mg of the title compound as its free base, m/e 709.0; HPLC RT: 16.38 minutes. A freshly prepared solution of acetyl chloride (30 mg, 0.387 mmol) in 3.0 ml of methanol was allowed to stand at room temperature for 90 minutes. The free base (120 mg, 0.169 mmol) was added, and the resulting solution was stirred under nitrogen for two hours. The volatile components were then evaporated under reduced pressure to give 136 mg of the title compound as an off white solid.

EXAMPLE 4

(Method D)

20-[3-(Dimethylamino)propylamino]-20-deoxorepromicin

Repromicin (18.00 g, 31.82 mmol) was dissolved in 300 ml of methanol. 3-(Dimethylamino)propylamine (8.00 ml, 63.63 mmol) was then added to the repromicin solution and the resulting reaction mixture was stirred at room temperature for 30 minutes. The reaction mixture was then cooled to 0° C. and glacial acetic acid (1.80 ml, 31.82 mmol) was added. After 10 minutes, sodium cyanoborohydride (2.00 g, 31.82 mmol) was added at 0° C. as a solution in 15 ml of methanol. The resulting reaction mixture was stirred at 0° C. for 1 hour and then concentrated under reduced pressure. The residue was taken up in 150 ml of ethyl acetate and 150 ml of saturated aqueous $NaHCO_3$. The two layers were separated and the aqueous layer was extracted with 2×150 ml of ethyl acetate. The combined organic layers were washed with 150 ml of brine, dried with anhydrous $Na_2SO_4$, and concentrated under reduced pressure. The crude product was purified by flash chromatography (gradient elution, 9:1 $CH_2Cl_2$/MeOH and then 9:1 $CH_2Cl_2$/MeOH with 1% $Et_3N$) to give 10.90 g of the desired product (53% yield), m/e, 653.0; HPLC RT: 28.63 minutes.

Alternatively, to a stirring solution of repromicin (10.0 g, 17.7 mmol) in methanol (88 mL) at room temperature was added 3-dimethylaminopropylamine (2.2 mL, 17.7 mmol). After about 30 minutes the solution was cooled to about 0° C., and sodium borohydride (267 mg, 7.1 mmol) was added. After stirring for about 2 hours at about 0° C., the mixture was concentrated to near dryness, taken up in chloroform, washed with saturated aqueous sodium bicarbonate and brine, dried ($Na_2SO_4$), filtered and concentrated. The crude product was subjected to column chromatography on silica gel, eluting with 1% $NH_4OH$/10% $MeOH/CHCl_3$, to afford 5.75 g. (50%) of the desired product, m/e, 653.0; HPLC RT: 28.63 minutes.

EXAMPLE 5

(Method E)

20-[3-(Dimethylamino)propyl(L-alanyl)amino]-20-deoxorepromicin

To a solution of N-t-BOC-L-alanine (4.1 g, 21.8 mmol), dicyclohexylcarbodiimide (4.5 g, 21.8 mmol) and hydroxybenzotriazole (2.95 g, 21.8 mmol) in dichloromethane (109 mL) at about 0° C. was added 20-[3-(dimethylamino)propylamino]-20-deoxorepromicin (14.2 g, 21.8 mmol.) The mixture was allowed to warm to room temperature, and was stirred for about 3 days. The mixture was filtered, and the solvent was removed with a rotary evaporator. The crude product was purified by flash chromatography on silica gel (gradient elution, 2% MeOH/0.25% $NH_4OH$ in chloroform to 4% MeOH/0.5% $NH_4OH$ in chloroform) to afford 10.02 g (53%) of the BOC-protected title product.

The BOC-protected material was dissolved in a mixture of trifluoroacetic acid and dichloromethane (1:1, 100 mL), and was stirred at about 0° C. for about 20 minutes. The solvent was removed with a rotary evaporator, and the residue was triturated with diethyl ether and was dried. This material was dissolved in water, and 1N NaOH was added to bring the solution to pH 10. The resulting aqueous phase was extracted with chloroform, dried over sodium sulfate, and concentrated to afford 8.59 g (97%) of the desired product, m/e 724; HPLC RT: 2.16 minutes.

EXAMPLE 6

(Method F)

20-N-[3-(L-Alanyl)amino-2,2-dimethylpropylamino]-20-deoxorepromicin trifluoroacetate To a stirring solution of 20-N-(3-amino-2,2-dimethylpropylamino)-20-deoxorepromicin (1.05 g, 1.60 mmol) in DMF (8 mL) at room temperature was added N-t-BOC-L-alanine hydroxysuccinimide ester (553 mg, 1.9 mmol). After about 6 hours, the solvent was removed with a rotary evaporator, and the residue was dissolved in chloroform, washed with brine, dried over sodium sulfate, and concentrated. The crude product was subjected to flash chromatography on silica gel (2% MeOH/0.25% $NH_4OH$ in $CH_2Cl_2$) to afford 471 mg (36%) of the BOC-protected title product.

The BOC-protected intermediate (453 mg, 0.55 mmol) was dissolved in a mixture of dichloromethane and trifluoroacetic acid (1:1, 10 mL) and was stirred at about 0°0 C. for about 15 minutes. The solvent was removed with a rotary evaporator, and the residue was triturated with diethyl ether and dried to afford the desired product as the trifluoroacetate salt in quantitative yield, m/e 724.0.

EXAMPLE 7

(Method G)

20-Cyano-20-dimethylamino-20-deoxorosaramicin hydrochloride

Rosaramicin (1.0 g, 1.72 mmol) and 54 mg of zinc iodide were added to a single neck round bottom flask. Enough anhydrous methanol was added to allow the mixture to stir easily. Trimethylsilylcyanide (0.3 mL, 2.15 mmol) was added in one portion; the resulting solution was stirred at room temperature for about 15 minutes. A 0.75M solution of dimethylamine in methanol (12 mL, 9.0 mmol) was added. The resulting solution was heated at about 40° C. for about two hours, and was then allowed to cool to room temperature. The volatile components were evaporated under reduced pressure to furnish 1.1 g of a yellow residue. This material was then purified by chromatography to give the free base of the title compound as a colorless solid: yield 388 mg (35%); HPLC RT: 10.16 minutes; m/e 636.

The hydrochloride was prepared by dissolving the free base of the title compound in methanol that had been previously treated with an equivalent amount of acetyl chloride. The solution was evaporated to dryness to furnish a solid: m.p. 112°–120° C.

EXAMPLE 8

(Method H)

20-Cyano-20-[3-(dimethylamino)propylamino]-20-deoxo-12,13-deepoxycirramycin $A_1$ A solution containing 325 mg (0.56 mmol) of deepoxycirramycin $A_1$ and 70 μl of -(dimethylamino)propylamine (0.56 mmol) in 5 mL of MeOH was cooled to about 0° C. Glacial acetic acid (32 μl, 0.56 mmol) was added at about 0° C., followed by $NaCNBH_3$ (35 mg, 0.56 mmol). The resulting reaction mixture was stirred at about 0° C. for about 1 hour. It was then poured into 20 mL saturated aqueous $NaHCO_3$ and extracted with ethyl acetate. The combined organic layers were washed with brine, dried ($Na_2SO_4$), and concentrated under reduced pressure. The crude product was purified by flash chromatography (90% $CH_2Cl_2$, 9% MEOH, 1% $Et_3N$) to give 0.85 mg of the title product. Mass Spec. 693.

EXAMPLE 9

( Method I)

20-Deoxo-20-[N-methyl-N-(L-seryl)amino]repromicin trifluoroacetate

A solution containing 100 mg of 20-deoxo-20-methylamino-repromicin (0.17 mmol) and 35 mg of BOC-L-serine (0.17 mmol) in 2 ml of anhydrous DMF was cooled to about 0° C. Diethyl cyanophosphate (0.19 mmol, 29 μl) was added at about 0° C., followed by anhydrous triethylamine (0.19 mmol, 26 μl). The resulting reaction mixture was stirred at about 0° C. for about 20 minutes. It was then poured into 15 ml of saturated aqueous $NaHCO_3$ and extracted with ethyl acetate. The combined organic layers were washed with brine, dried over $Na_2SO_4$, and concentrated under reduced pressure. The crude product was purified by flash chromatography ($CHCl_3$/MeOH/$NH_4OH$: 89:10:1). The purified product was dissolved in 1 ml of $CH_2Cl_2$ and cooled to 0° C. Anhydrous TFA (1 ml) was then added and the resulting reaction mixture was stirred at 0° C. for 30 minutes. It was then concentrated under reduced pressure, triturated with $Et_2O$, filtered, and dried to give 53 mg of the product as the TFA salt.

EXAMPLES 10–20

Compounds of Examples 10–20 having the general formula

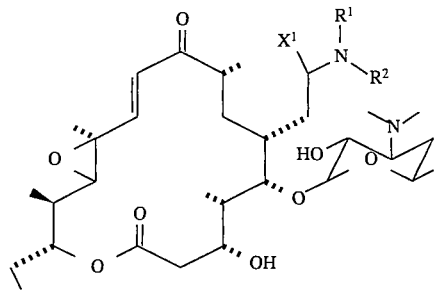

were prepared according to the method shown.

| Example No. | $NR^1R^2$ | $X^1$ | Prep'n Method | *Mass Spec. | RT (min) |
|---|---|---|---|---|---|
| 10 | methylamino | H | B | 597 | N.T. |
| 11 | diethylamino | H | A | 639 | 9.75 |
| 12 | dipropylamino | H | A | 667 | 21.06 |
| 13 | dibutylamino | H | A | 695 | 46.83 |
| 14 | piperidino | H | A | 651 | 10.55 |
| 15 | hexahydroazepin-1-yl | H | A | 665 | 14.42 |
| 16 | azetidin-1-yl | H | A | 624 | 9.66 |
| 17 | 3-(dimethylamino)propylamino | H | D | 669 | N.T. |
| 18 | N-[3-(dimethylamino)propyl]-N-methylamino | H | C | 683 | N.T. |
| 19 | pyrrolidino | —CN | G | 662 | 4.90 |
| 20 | morpholino | —CN | G | 678 | 12.48 |

N.T. = not taken
*Mass Spectra were obtained by either fast atom bombardment or electron impact method.

EXAMPLES 21–118

Compounds of Examples 21–118 having the general formula

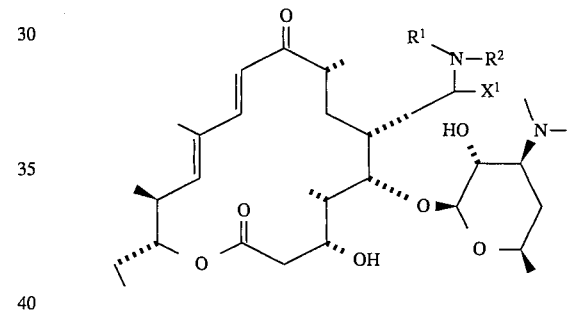

were prepared according to the method shown.

| Example No. | $NR^1R^2$ | $X^1$ | Prep'n Method | *Mass Spec. | RT (min) |
|---|---|---|---|---|---|
| 21 | 2-(morpholino)ethylamino | H | D | 681 | 16.03 |
| 22 | 3-(morpholino)propylamino | H | D | 695 | 15.57 |
| 23 | 2-(piperidino)ethylamino | H | D | 679 | 39.03 |
| 24 | 2-(dimethylamino)ethylamino | H | D | 639 | 23.49 |
| 25 | N-[3-(dimethylamino)propyl]-N-methylamino | H | A | 667 | 34.45 |
| 26 | N-[2-(dimethylamino)ethyl]-N-methylamino | H | C | 653 | 25.61 |
| 27 | N-[2-(piperidino)ethyl]-N-methylamino | H | C | 693 | 36.18 |
| 28 | 2-(pyrrolidino)ethylamino | H | D | 665 | 32.96 |
| 29 | 4-(dimethylamino)butylamino | H | D | 667 | N.T. |
| 30 | 5-(dimethylamino)pentylamino | H | D | 681 | N.T. |
| 31 | (pyridin-2-yl)methylamino | H | D | 660 | 22.16 |
| 32 | 2-(imidazol-4-yl)ethylamino | H | D | 662 | 9.80 |
| 33 | 4-(ethoxycarbonyl)piperazin-1-yl | H | A | N.T. | N.T. |
| 34 | 4-(hydroxy)butylamino | H | B | 640 | 9.48 |
| 35 | 3-(methoxy)propylamino | H | B | 640 | 15.21 |
| 36 | 3-(hydroxy)azetidin-1-yl | H | D | N.T. | N.T. |
| 37 | 3-amino-2,2-(dimethyl)propylamino | H | D | 652 | N.T. |
| 38 | (3aS,4R,5R,6S,7R,7aR)-hexahydro-4,6,7-trihydroxybenzo[d]-1,3-dioxolan-5-ylamino | H | D | 741 | 4.11 |
| 39 | 4-(amino)butylamino | H | B | 624 | N.T. |

-continued

| Example No. | NR¹R² | X¹ | Prep'n Method | *Mass Spec. | RT (min) |
|---|---|---|---|---|---|
| 40 | 4-(amino)cyclohexylamino | H | D | N.T. | N.T. |
| 41 | trans,trans 2,6-dihydroxy-cyclohexylamino | H | D | 681 | 12.94 |
| 42 | 2-[2-(methoxy)ethoxy]ethylamino | H | D | N.T. | 15.55 |
| 43 | cis-2-(amino)cyclohexylamino | H | D | 665 | N.T. |
| 44 | 2-S-1,3-dihydroxy-3-phenyl-2-propylamino | H | D | 717 | N.T. |
| 45 | 2-S-1-hydroxy-3-(imidazol-4-yl)-2-propylamino | H | D | 691 | N.T. |
| 46 | 2-cyanoethylamino | H | D | 619 | 9.83 |
| 47 | 1-(hydroxymethyl)-cyclopentyl amino | H | D | 664 | 18.46 |
| 48 | N-[3-(dimethylamino)propyl]-N-(glycyl)amino | H | E | 710 | N.T. |
| 49 | N-[3-(dimethylamino)propyl]-N-(L-valyl)amino | H | E | 751 | N.T. |
| 50 | N-[3-(N'-L-alanyl-N'-methyl-amino)propyl]-N-methylamino | H | E | 723 | N.T. |
| 51 | N-{3-[N'-(L-alanyl)amino]-propyl}-N-(L-alanyl)amino | H | F** | 766 | N.T. |
| 52 | N-{3-[N'-(L-alanyl)amino]-propyl}amino | H | D† | 695 | N.T. |
| 53 | N-(3-aminopropyl)-N-(L-alanyl)-amino | H | Fγ | 695 | N.T. |
| 54 | 2-hydroxyethylamino | H | D | 611 | N.T. |
| 55 | 2,3-(R,S)-dihydroxypropylamino | H | D | 641 | N.T. |
| 56 | 3-[bis(hydroxyethyl)amino]-propylamino | H | D | 712 | N.T. |
| 57 | 2,2-dimethyl-3-hydroxypropyl-amino | H | D | 653 | 11.32 |
| 58 | 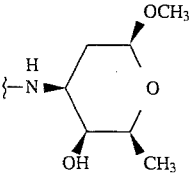 | H | D | 711 | N.T. |
| 59 | 2-S-(hydroxymethyl)pyrrolidino | H | A | 651 | N.T. |
| 60 | bis(2-hydroxyethyl)amino | H | A | 655 | N.T. |
| 61 | 1,3-dihydroxyprop-2-yl-amino | H | D | 641 | N.T. |
| 62 | N-[2-hydroxyethyl]-N-methyl-amino | H | A | 625 | N.T. |
| 63 | (1RS,3S,4R,5R)-3,4,5-trihydroxy-cyclohexylamino | H | D | 697 | N.T. |
| 64 | 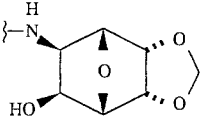 | H | D | 723 | N.T. |
| 65 | 2-S-(carboxy)-pyrrolidin-1-yl | H | A | 665 | 4.96 |
| 66 | dimethylamino | CN | G | 593 (M − CN) | 9.12 |
| 67 | pyrrolidino | CN | G | 646 | 8.43 |
| 68 | morpholino | CN | G | 635 | 19.35 |
| 69 | N-(3-aminopropyl)-N-(2-hydroxyethyl)amino | H | A | 668 | N.T. |
| 70 | 3-(2-hydroxyethylamino)-propyl-amino | H | D | 669 | N.T. |
| 71 | N-[3-(dimethylamino)propyl]-N-(L-phenylalanyl)amino | H | E | 799 | N.T. |
| 72 | N-[3-(N'-glycyl-N'-methylamino)-propyl]-N-methylamino | H | E | 709 | N.T. |
| 73 | N-[3-(N'-β-alanyl-N'-methyl-amino)propyl]-N-methylamino | H | E | 723 | N.T. |
| 74 | N-[3-(N'-sarcosyl-N'-methyl-amino)propyl]-N-methylamino | H | E | 723 | N.T. |
| 75 | N-[3-(N'-L-valyl-N'-methyl-amino)propyl]-N-methylamino | H | E | 751 | N.T. |
| 76 | N-[3-(N'-L-phenylalanyl-N'-methylamino)propyl]-N-methyl- | H | E | 800 | N.T. |

-continued

| Example No. | NR¹R² | X¹ | Prep'n Method | *Mass Spec. | RT (min) |
|---|---|---|---|---|---|
|  | amino |  |  |  |  |
| 77 | N-[3-(N'-D-alanyl-N'-methyl-amino)propyl]-N-methylamino | H | E | 723 | N.T. |
| 78 | N-[3-(N'-L-leucyl-N'-methyl-amino)propyl]-N-methylamino | H | E | 763 | N.T. |
| 79 | N-[3-(N'-L-seryl-N'-methyl-amino)propyl]-N-methylamino | H | E | 739 | N.T. |
| 80 | N-[3-(dimethylamino)propyl]-N-[4-(dimethylamino)butyryl]amino | H | I | 764 | N.T. |
| 81 | N-[3-(dimethylamino)propyl]-N-[3-(diethylamino)propionyl]-amino | H | I | 778 | N.T. |
| 82 | N-[3-(dimethylamino)propyl]-N-(glycyl-glycyl)amino | H | I | 765 | N.T. |
| 83 | N-[3-(dimethylamino)propyl]-N-(L-alanyl-L-alanyl)amino | H | I | 793 | N.T. |
| 84 | N-[3-(dimethylamino)propyl]-N-(acetyl)amino | H | E | 694 | N.T. |
| 85 | N-[3-(dimethylamino)propyl]-N-(D-alanyl)amino | H | E | 723 | N.T. |
| 86 | N-[3-(dimethylamino)propyl]-N-(L-seryl)amino | H | E | 739 | N.T. |
| 87 | N-[3-(dimethylamino)propyl]-N-(2-aminobutyryl)amino | H | E | 737 | N.T. |
| 88 | N-[3-(dimethylamino)propyl]-N-(sarcosyl)amino | H | E | 723 | N.T. |
| 89 | N-[3-(dimethylamino)propyl]-N-(N,N-dimethylglycyl)amino | H | E | 737 | N.T. |
| 90 | N-[3-(dimethylamino)propyl]-N-(L-lysyl)amino | H | E | 780 | N.T. |
| 91 | N-[3-(N'-L-lysyl-N'-methylamino)-propyl]-N-methylamino | H | E | 780 | N.T. |
| 92 | N-[3-(N'-2-aminobutyryl-N'-methylamino)propyl]-N-methylamino | H | E | 737 | N.T. |
| 93 | N-[3-(N'-glycylglycyl-N'-methylamino)propyl]-N-methylamino | H | E | 766 | N.T. |
| 94 | N-[3-(N'-2,2-dimethylglycyl-N'-methylamino)propyl]-N-methylamino | H | E | 737 | N.T. |
| 95 | N-[N'-[4-(dimethyl-amino)butyryl]-N'-methyl-3-aminopropyl]-N-methylamino | H | E | 765 | N.T. |
| 96 | N-[N'-[3-(diethyl-amino)propionyl]-N'-methyl-3-aminopropyl]-N-methylamino | H | E | 779 | N.T. |
| 97 | N-[3-(dimethylamino)propyl]-N-(L-tryptophyl)amino | H | I | 838 | N.T. |
| 98 | N-[3-(dimethylamino)propyl]-N-(L-phenylglycyl)amino | H | I | 785 | N.T. |
| 99 | N-[3-(dimethylamino)propyl]-N-(L-tyrosyl)amino | H | I | 815 | N.T. |
| 100 | N-[3-(dimethylamino)propyl]-N-(D-4-hydroxyphenylglycyl)amino | H | I | 801 | N.T. |
| 101 | N-methyl-N-(L-lysyl)amino | H | I | 709 | N.T. |
| 102 | N-methyl-N-(L-ornithyl)amino | H | I | 695 | N.T. |
| 103 | N-methyl-N-(L-threonyl)amino | H | I | 682 | N.T. |
| 104 | 1-(L-alanyl)-4-piperazinyl | H | I | 707 | N.T. |
| 105 | 1-(L-seryl)-4-piperazinyl | H | I | 723 | N.T. |
| 106 | N,N-bis-[3-(diethylamino)-propyl]amino | H | A | 793 | N.T. |
| 107 | N,N-bis-[3-(dimethylamino)-propyl]amino | H | A | 738 | N.T. |
| 108 | N-[2-(N'-L-alanyl-N'-methyl-amino)ethyl]-N-methylamino | H | E | 710 | N.T. |
| 109 | N-[2-(N'-glycyl-N'-methylamino)-ethyl]-N-methylamino | H | E | 696 | N.T. |
| 110 | N-[2-(methylamino)ethyl]-N-methylamino | H | A | 634 | N.T. |
| 111 | N-[4-(dimethylamino)butyl]-N-(glycyl)amino | H | E | 723 | N.T. |
| 112 | N-[3-(dimethylamino)propyl]-N-(L-glutamyl)amino | H | E | 781 | N.T. |
| 113 | N-[4-(dimethylamino)butyl]-N-(L-alanyl)amino | H | E | 737 | N.T. |
| 114 | N-[4-(dimethylamino)butyl]-N-(L- | H | E | 765 | N.T. |

-continued

| Example No. | NR¹R² | X¹ | Prep'n Method | *Mass Spec. | RT (min) |
|---|---|---|---|---|---|
| 115 | valyl)amino<br>N-[4-(dimethylamino)butyl]-N-(L-phenylalanyl)amino | H | E | 813 | N.T. |
| 116 | N-[2-(dimethylamino)ethyl]-N-(L-alanyl)amino | H | E | 709 | N.T. |
| 117 | N-[2-(dimethylamino)ethyl]-N-(glycyl)amino | H | E | 695 | N.T. |
| 118 | N-[2-(dimethylamino)ethyl]-N-(L-seryl)amino | H | E | 725 | N.T. |

N.T. = not taken
*Mass Spectra were obtained by either fast atom bombardment or electron impact method.
**Using 20-N-(3-aminopropylamino)-20-deoxorepromicin and two equivalents of N-t-BOC-L-alanine hydroxysuccinimide ester.
†Using 3-N'-(N-t-BOC-L-alanyl)aminopropylamine; reductive amination was followed by BOC deprotection (TFA).
ᵞUsing 20-N-(3-N'-t-BOC-aminopropylamino)-20-deoxorepromicin.

EXAMPLES 119–153

Compounds of Examples 119–153 having the general formula

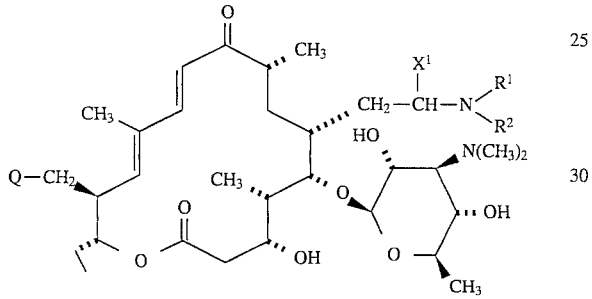

were prepared according to the method shown.

| Example No. | Q | NR¹R² | X¹ | Prep'n Method | ¹Mass Spec. | HPLC RT (min) |
|---|---|---|---|---|---|---|
| 119 | HO— | 3-(dimethylamino)propylamino | H | B* | 684 | 13.19 |
| 120 | 1,2,3,6-tetrahydropyridin-1-yl | N-[3-(dimethylamino)propyl]-N-methylamino | H | A** | 763 | N.T. |
| 121 | HO— | N-[3-(dimethylamino)propyl]-N-methylamino | H | A* | 698 | N.T. |
| 122 | 2-hydroxyethyl-(methyl)-amino | 3-(dimethylamino)propylamino | H | B** | 742 | N.T. |
| 123 | 2-hydroxyethyl-(methyl)-amino | trans, trans-2,6-dihydroxycyclohexylamino | H | B** | 771 | N.T. |
| 124 | 2-hydroxyethyl-(methyl)-amino | N-[3-(dimethylamino)propyl-N-methylamino | H | A** | 756 | N.T. |
| 125 | 1,2,3,6-tetrahydropyridin-1-yl | 3-(dimethylamino)propylamino | H | B** | 749 | N.T. |
| 126 | 1,2,3,6-tetrahydropyridin-1-yl | 3-amino-2,2-(dimethyl)-propylamino | H | B** | 749 | N.T. |
| 127 | 1,2,3,6- | trans, trans-2,6- | H | B** | 779 | N.T. |

-continued

| Example No. | Q | NR$^1$R$^2$ | X$^1$ | Prep'n Method | $^1$Mass Spec. | HPLC RT (min) |
|---|---|---|---|---|---|---|
|  | tetrahydro-pyridin-1-yl | dihydroxy-cyclohexylamino |  |  |  |  |
| 128 | piperidin-1-yl | N-[3-(dimethyl-amino)propyl]-N-methylamino | H | A** | 765 | N.T. |
| 129 | pyrrolidin-1-yl | N-[3-(dimethyl-amino)propyl]-N-methylamino | H | A** | 751 | N.T. |
| 130 | N,N-diethyl-amino | N-[3-(dimethyl-amino)propyl]-N-methylamino | H | A** | 753 | N.T. |
| 131 | N,N-di-propyl-amino | N-[3-(dimethyl-amino)propyl]-N-methylamino | H | A** | 781 | N.T. |
| 132 | homo-piperidinyl | N-[3-dimethyl-amino)propyl]-N-methylamino | H | A** | 780 | N.T. |
| 133 | homo-piperidinyl | 3-(dimethyl-amino)propyl-amino | H | B** | 766 | N.T. |
| 134 | homo-piperidinyl | trans, trans-2,6-dihydroxy-cyclohexylamino | H | B** | 795 | N.T. |
| 135 | homo-piperidinyl | 3-amino-2,2-(dimethyl)-propylamino | H | B** | 766 | N.T. |
| 136 | homo-piperidinyl | N-[3-(dimethyl-amino)propyl]-N-(L-alanyl)amino | H | F** | 837 | N.T. |
| 137 | N,N-dimethyl-amino | 3-(dimethyl-amino)propyl-amino | H | D** | 711 | N.T. |
| 138 | N,N-dimethyl-amino | N-[3-(dimethyl-amino)propyl]-N-methylamino | H | A** | 725 | N.T. |
| 139 | N,N-dimethyl-amino | trans, trans-2,6-dihydroxy cyclohexylamino | H | D** | 740 | N.T. |
| 140 | N,N-dimethyl-amino | 3-(piperidino)-propylamino | H | D** | 751 | N.T. |
| 141 | morpholino | 3-(dimethyl-amino)propyl-amino | H | D** | 753 | N.T. |
| 142 | morpholino | N-[3-(dimethyl-amino)propyl]-N-methylamino | H | A** | 767 | N.T. |
| 143 | morpholino | 2,2-dimethyl-3-amino-1-propyl-amino | H | D** | 754 | N.T. |
| 144 | morpholino | trans, trans-2,6-dihydroxy-1-cyclohexylamino | H | D** | 782 | N.T. |
| 145 | morpholino | N-[3-(dimethyl-amino)propyl]-N-(L-alanyl)-amino | H | E** | 824 | N.T. |
| 146 | 2,6-dimethyl-morpholin-4-yl | N-[3-(dimethyl-amino)propyl]-N-methylamino | H | A** | 795 | N.T. |
| 147 | 2,6-dimethyl-morpholin-4-yl | N-[3-(diethyl-amino)propyl]-N-methylamino | H | A** | 810 | N.T. |
| 148 | ![structure: H3C-C(=O)-O-cyclohexyl with CH3, OCH3, OCH3 substituents, O-linkage] | N-[3-(dimethyl-amino)propyl]-N-methylamino | H | A** | 914 | N.T. |
| 149 | morpholino | N-[3-(dimethyl-amino)propyl]-N-(L-alanyl)amino | H | E** | 824 | N.T. |

-continued

| Example No. | Q | NR¹R² | X¹ | Prep'n Method | ¹Mass Spec. | HPLC RT (min) |
|---|---|---|---|---|---|---|
| 150 | phenoxy | N-[3-(dimethyl-amino)propyl]-N-methylamino | H | A** | 773 | N.T. |
| 151 | 2-pyridyloxy | N-[3-(dimethyl-amino)propyl]-N-methylamino | H | A** | 774 | N.T. |
| 152 | 4-pyridyloxy | N-[3-(dimethyl-amino)propyl]-N-methylamino | H | A** | 774 | N.T. |
| 153 | 3-(dimethyl-amino)-phenoxy | N-[3-(dimethyl-amino)propyl]-N-methylamino | H | A** | 816 | N.T. |

N.T. = not taken
[1]Mass Spectra were obtained by either fast atom bombardment or electron impact method.
*Starting with 5-mycaminosyltylonolide.
**Using 20-N-(3-aminopropylamino)-20-deoxorepromicin and two equivalents of N-t-BOC-L-alanine hydroxysuccinimide ester.

EXAMPLES 154–188

Compounds of Examples 154–188 having the general formula

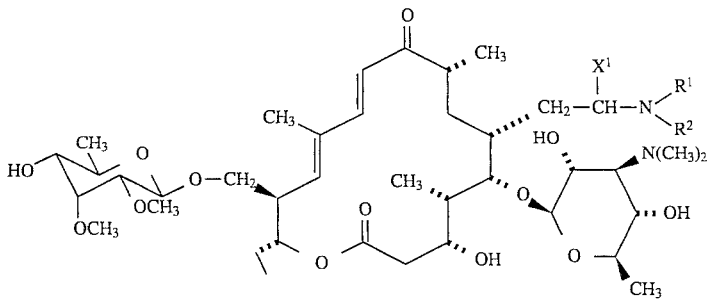

were prepared according the method shown

| Example No. | NR¹R² | X¹ | Prep'n Method | *Mass Spec. | RT (Min) |
|---|---|---|---|---|---|
| 154 | N-[3-(dimethylamino)-propyl]-N-methylamino | H | A | 872 | N.T. |
| 155 | 4-(dimethylamino)-butylamino | H | D | 888 | N.T. |
| 156 | 4-(hydroxy)butylamino | H | D | 845 | N.T. |
| 157 | 2-(morpholino)ethyl-amino | H | D | 886 | N.T. |
| 158 | N,N-bis(2-hydroxyethyl)amino | H | A | 861 | N.T. |
| 159 | 1,3-dihydroxy-2-propyl-amino | H | D | 847 | N.T. |
| 160 | 2-(hydroxy)ethylamino | H | D | 817 | N.T. |
| 161 | 2-S-1(imidazol-4-yl)-3-hydroxy-2-propylamino | H | D | 897 | N.T. |
| 162 | 2-S-1,3-dihydroxy-1-phenyl-2-propylamino | H | D | 923 | N.T. |
| 163 | 3-amino-2,2-dimethyl-1-propylamino | H | D | 858 | N.T. |
| 164 | 3-(dimethylamino)-propylamino | H | D | 858 | N.T. |
| 165 | N-[2-(diisopropyl-amino)ethyl]-N-(L-alanyl)amino | H | E | 971 | N.T. |
| 166 | N-[(2-piperidin-1-yl)-ethylamino]-N-(L-alanyl)amino | H | E | 955 | N.T. |
| 167 | N-[2-pyrrolidin-1-yl)-ethylamino]-N-(L-alanyl)amino | H | E | 941 | N.T. |
| 168 | N-[3-(dimethylamino)-propyl]-N-(L-alanyl)-amino | H | E | N.T. | N.T. |
| 169 | 3-(diethylamino)-propylamino | H | D | 886 | N.T. |
| 170 | N-[3-(diethylamino)-propyl]-N-methylamino | H | A | 900 | N.T. |
| 171 | N-[2-(dimethylamino)-ethyl]-N-methylamino | H | A | 858 | N.T. |
| 172 | N-[2-(diethylamino)-ethyl]-N-methylamino | H | A | 887 | N.T. |
| 173 | N-[2-(N-methyl-N-benzylamino)ethyl]-N-methylamino | H | A | 934 | N.T. |
| 174 | N-2-(diisopropyl-amino)ethylamino | H | D | 900 | N.T. |
| 175 | trans-4-amino-cyclohexylamino | H | D | 870 | N.T. |
| 176 | 2-(pyrrolidin-1-yl)-ethylamino | H | D | 870 | N.T. |
| 177 | 2-(piperidin-1-yl)-ethyl-amino | H | D | 884 | N.T. |
| 178 | N-[3-(dimethylamino)-propyl]-N-ethylamino | H | A | 886 | N.T. |
| 179 | N-[3-(ethylamino)- | H | A | 886 | N.T. |

-continued

| Example No. | NR¹R² | X¹ | Prep'n Method | *Mass Spec. | RT (Min) |
|---|---|---|---|---|---|
| | propyl]-N-ethylamino | | | | |
| 180 | N-[2-(N-methyl-N-propylamino)ethyl]-N-propylamino | H | A | 928 | N.T. |
| 181 | N-[2-(diisopropyl-amino)-ethyl]-N-(L-alanyl)amino | H | E | 971 | N.T. |
| 182 | N-[2-(piperidin-1-yl)-ethyl]-N-(L-alanyl)-amino | H | E | 955 | N.T. |
| 183 | N-[(2-pyrrolidin-1-yl)-ethyl]-N-(L-alanyl)-amino | H | E | 941 | N.T. |
| 184 | N-[3-(dimethylamino)-propyl]-N-(L-alanyl)-amino | H | E | 929 | N.T. |
| 185 | N,N-bis-[3-(dimethyl-amino)propyl]amino | H | A | 943 | N.T. |
| 186 | N,N-bis-[3-(diethyl-amino)propyl]amino | H | A | 999 | N.T. |
| 187 | N-[3-(dimethyl-amino)propyl]-N-(glycyl)amino | H | E | 915 | N.T. |
| 188 | N-[2-(dimethylamino)-ethyl]-N-benzylamino | H | A | 934 | N.T. |

N.T. = not taken
*Mass Spectra were obtained by either fast atom bombardment or electron impact method.

EXAMPLE 189

20-(Dimethylaminomethyl)-20-deoxorepromicin

Potassium tert-butoxide (233 mg, 1.99 mmol) was added in a single portion, at room temperature and under a nitrogen atmosphere, to a suspension of (methoxymethyl)triphenylphosphonium chloride (682 mg, 1.99 mmol) and 8 ml of anhydrous 1,4-dioxane. The resulting reaction mixture was stirred for 20 minutes. A solution containing repromicin (450 mg, 0.795 mmol) in 6 ml of 1,4-dioxane was then added to the freshly generated ylid solution. The resulting mixture was stirred for three hours, diluted with 30 ml of water, and then extracted with three 30 ml portions of ethyl acetate. The combined organic layers were washed with three 20 ml portions of saturated aqueous sodium chloride (brine), dried over anhydrous sodium sulfate, filtered, and concentrated under reduced pressure. The resulting residue was dissolved in a solution of 6 ml of tetrahydrofuran and 3 ml of 1N hydrochloric acid. The resulting solution was stirred at room temperature for four hours. It was then diluted with 10 ml of saturated aqueous sodium bicarbonate, and extracted with three 10 ml portions of ethyl acetate. The combined extracts were washed with 20 ml of brine, dried over sodium sulfate, and concentrated under reduced pressure. Chromatography on silica gel, eluant: 8:2 dichloromethane/methanol, afforded 200 mg (43%) of 20-deoxo-2-formylrepromicin HPLC RT: 13.91 minutes.

A solution of 20-deoxo-20-formylrepromicin (300 mg, 0.517 mmol) in 5.0 ml of ethyl acetate was treated first with 2.07 ml of 0.5M dimethylamine in methanol, and then with 39 μl (1.03 mmol) of formic acid. The resulting solution was heated at 70°–75° C. for three hours. Upon cooling to room temperature, the reaction solution was diluted with 15 ml of ethyl acetate. The organic phase was then washed with two 5 ml portions of aqueous saturated sodium bicarbonate, once with 5 ml of brine, dried over anhydrous sodium sulfate, and concentrated. The residue was chromatographed on silica gel eluant: 8:2 dichloromethane/methanol to 8:2 dichloromethane/methanol plus 1% triethylamine. There was obtained 180 mg (57%) of the title compound, HPLC RT: 14.36 minutes.

EXAMPLE 190

20-(Azetidin-1-yl-methyl)-20-deoxorepromicin

Employing the procedure described in Example 189 with azetidine replacing dimethylamine afforded the title compound, HPLC RT: 13.45 minutes.

EXAMPLE 191

20-Cyano-20-[3-(dimethylamino)propylamino]-20-deoxo-12,13-deepoxy-23-(hexahydoazepin-1-yl)cirramycin $A_1$)

In a manner analogous to that described in Example 8, method H, the title compound was prepared using 23-(hexahydroazepin-1-yl)deepoxycirramycin $A_1$ in place of deepoxycirramycin $A_1$:m/e 883.

EXAMPLE 192

20-Cyano-20-deoxo-20-[2-(pyrrolidino)ethylamino]desmycosin

In a manner analogous to that described in Example 8, method H, the title compound was prepared using desmycosin in place of deepoxycirramycin $A_1$ and 2-(pyrrolidino)ethylamine in place of N,N,N'-trimethyl-1,3-propanediamine: m/e 895.

EXAMPLE 193

20-Cyano-20-deoxo-20-[3-(dimethylamino)propylamino]desmycosin

In a manner analogous to that described in Example 8, method H, the title compound was prepared using desmycosin in place of deepoxycirramycin $A_1$: m/e 883.

EXAMPLE 194

20-Cyano-20-deoxo-20-[(2-hydroxyethyl)amino]desmycosin

In a manner analogous to that described in Example 8, method H, the title compound was prepared using desmycosin in place of deepoxycirramycin $A_1$ and 2-aminoethanol in place of N,N,N'-trimethyl-1,3-propanediamine: m/e 842.

EXAMPLE 195

20-Cyano-20-deoxo-20-[(2-fluoroethyl)amino]desmycosin

In a manner analogous to that described in Example 8, method H, the title compound was prepared using desmycosin in place of deepoxycirramycin $A_1$ and 2-fluoroethylamine in place of N,N,N'-trimethyl-1,3-propanediamine: m/e 844.

EXAMPLE 196

20-[N-Methyl-N-(3-dimethylamino)propylamino]-20-deoxo-4'-deoxymycaminosyl tylonolide In a manner analogous to that described in Example 1, Method A, the title compound was prepared using 4'-deoxymycaminosyl tylonolide and N,N,N'-trimethyl-1,3-propane diamine: m/e 681.

EXAMPLE 197

20-[N-(4-Dimethylaminobutyl)amino]-20-deoxo-4'-deoxymycaminosyl tylonolide

In a manner analogous to that described in Example 2, Method B, the title compound was prepared using 4'-deoxymycaminosyl tylonolide and N-[4-(dimethylamino)butyl] amine: m/e 681.

EXAMPLE 198

20-[N-3-(Glycylamino)propyl-N-(2-hydroxyethyl)amino]-20-deoxorepromicin

To a solution of 20-[N-(3-aminopropyl)-N-(2-hydroxyethyl)amino]-20-deoxorepromicin (150 mg, 0.23 mmol) and N-t-BOC-glycine (39 mg, 0.23 mmol) in acetonitrile (2 mL) at ambient temperature was added 2-ethoxy-1-ethoxycarbonyl-1,2-dihydroquinoline (EEDQ). After having been stirred overnight, the solvent was removed ith a rotary evaporator. The residue was dissolved in $CH_2Cl_2$ and washed with aqueous saturated $NaHCO_3$. The aqueous layer was extracted with a second portion of $CH_2Cl_2$. The combined organic layers were dried over $Na_2SO_4$, filtered, and concentrated. The crude product was purified by flash chromatography on silica gel (7% MeOH/0.4% $NH_4OH$ in $CH_2Cl_2$) to afford 109 mg (59%) of the BOC-protected title product.

The BOC-protected material was dissolved in a solution of trifluoroacetic acid (1 mL) and $CH_2Cl_2$ (1.5 mL), and was stirred at about 0° C. for about 1 hour. The solvents were removed by rotary evaporator. The resulting oil was adjusted to pH≧9 with aqueous saturated $NaHCO_3$ and 1N NaOH, followed by extraction (2x) with $CH_2Cl_2$. The combined organic layers were dried over $Na_2SO_4$, filtered, and concentrated to provide 70 mg (82%) of desired product, m/e 725.

EXAMPLE 199

20-Deoxo-20-[N-(3-dimethylamino)propyl-N-(L-histidinyl)amino]-repromicin trifluoroacetate A solution containing 200 mg of 20-deoxo-20-(3-dimethylamino)propylamino repromicin (0.31 mmol) and 78 mg of N-BOC-L-histidine (0.31 mmol) in 2 ml of anhydrous DMF was cooled to about 0° C. Diphenyl phosphorylazide (73 µl, 0.34 mmol) was added at about 0° C., followed by anhydrous triethylamine (51 µl, 0.37 mmol). The resulting reaction mixture was stirred at about 0° C. for about 5 hours. It was then warmed to room temperature and stirred for about 30 minutes. At this point, the reaction mixture was quenched with 15 ml of saturated aqueous $NaHCO_3$ and extracted with ethyl acetate. The combined organic layers were washed with brine, dried ($Na_2SO_4$), and concentrated under reduced pressure. The crude product was purified by flash chromatography ($CHCl_3$/MEOH/$NH_4OH$:89:10:1 ). The purified product was dissolved in 2 ml of $CH_2Cl_2$ and cooled to about 0° C. Anhydrous TFA (2 ml) was added. The resulting reaction mixture was stirred at about 0° C. for about 30 minutes. It was then concentrated under reduced pressure, triturated with $Et_2O$, filtered, and dried to give 86 mg of the product as the TFA salt.

We claim:

1. A compound of formula I

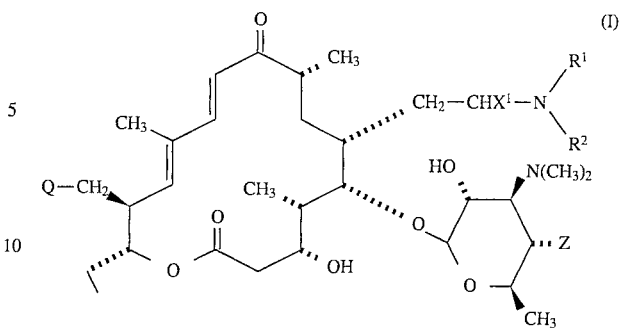

or a pharmaceutically acceptable salt thereof, wherein $X^1$ is H or CN;

Z is H or OH;

Q is selected from the group consisting of hydrogen,

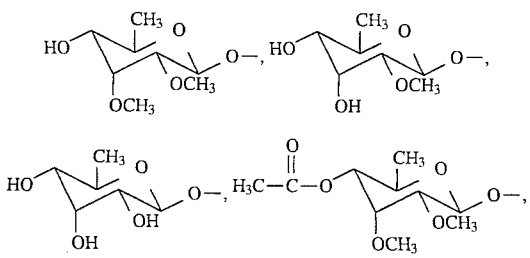

pyrrolidin-1-yl, piperidin-1-yl, homopiperidin-1-yl, N,N-diethylamino, N,N-dimethylamino, N,N-dipropylamino and

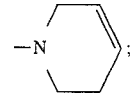

$R^1$ is selected from the group consisting of hydrogen, alkyl having 1 to 4 carbons, hydroxyalkyl having 2 to 4 carbons, and alkoxyalkyl having 2 to 4 carbons in the alkyl portion and 1 to 4 carbons in the alkoxy portion;

$R^2$ is substituted alkyl having 2 to 5 carbons, wherein the substituted alkyl is substituted with 1 or 2 substituents independently selected from the group consisting of amino, N-alkylamino having 1 to 4 carbons and N,N-dialkylamino having a total of 2 to 6 carbons.

2. A compound of formula II

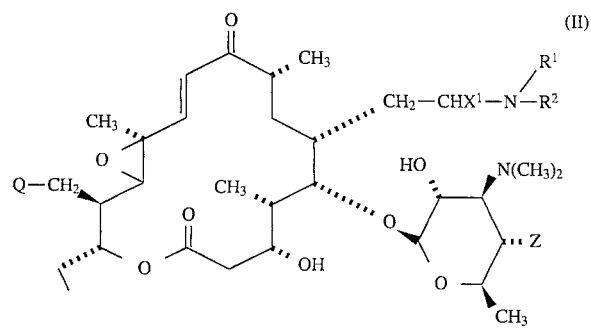

or a pharmaceutically acceptable salt thereof, wherein $X^1$ is hydrogen or CN; Z is hydrogen or hydroxy;

$R^1$ is selected from the group consisting of hydrogen, alkyl having 1 to 4 carbons, and alkoxyalkyl having 2 to 4 carbons in the alkyl portion and 1 to 4 carbons in the alkoxy portion;

$R^2$ is selected from the group consisting of hydrogen, alkyl having 1 to 4 carbons and substituted alkyl having 2 to 5 carbons, where the substituents are selected from the group consisting of hydroxy, alkoxy having 1 to 4 carbons, amino, N-alkylamino having 1 to 4 carbons, and N,N-dialkylamino having a total of 2 to 6 carbons; or $R^1$ and $R^2$ are taken together with the nitrogen to which they are attached and form a heterocyclic group selected from the group consisting of azetidinyl, pyrrolidino, piperidino, hexahydroazepinyl, and morpholino; and Q is hydrogen.

3. A compound of formula I

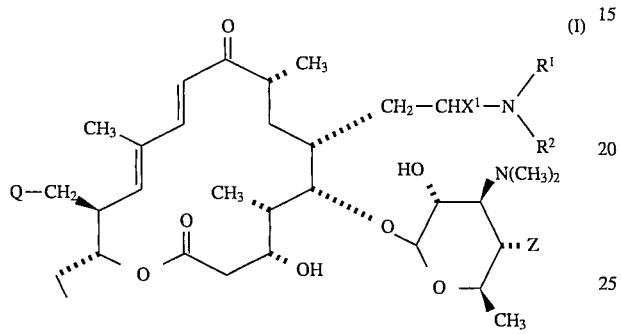

or a pharmaceutically acceptable salt thereof
wherein $X^1$ is H or CN;
Z is H or OH;
Q is selected from the group consisting of H, OH, fluoro, chloro, bromo, iodo, $OX^2$, $SX^2$,

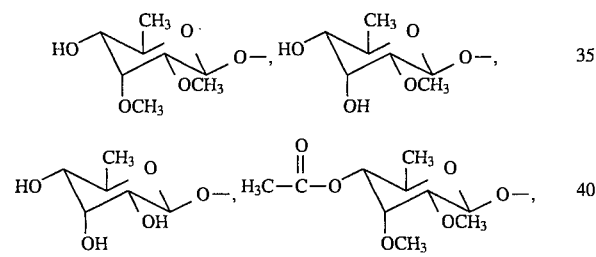

azetidin-1-yl, pyrrolidin-1-yl, piperidin-1-yl, 3,3-dimethylpiperidin-1-yl, hexahydroazepin-1-yl, octahydroazocin-1-yl, octahydroindol-1-yl, 1,3,3a,4,7,7a-hexahydroisoindol-2-yl, decahydroquinol-1-yl, decahydroisoquinol-2-yl, 1,2,3,4-tetrahydroisoquinol-2-yl, 1,2,3,6-tetrahydropyridin-1-yl, 4-alkylpiperazin-1-yl having 1 to 4 carbons in the alkyl portion, morpholino, 2,6-dimethylmorpholin-4-yl, thiomorpholino, and

where $R^3$ and $R^4$ are independently selected from the group consisting of H, alkyl having 1 to 4 carbons, hydroxyalkyl having 2 to 4 carbons, cycloalkyl having 3 to 8 carbons, alkenyl having 3 or 4 carbons, alkoxyalkyl having 1 to 4 carbons in the alkoxy portion and 2 to 4 carbons in the alkyl portion and alkoxyalkoxyalkyl having 1 to 4 carbons in each of the alkoxy portions and 2 to 4 carbons in the alkyl portion; and $X^2$ is selected from the group consisting of optionally substituted alkyl having 1 to 4 carbons, optionally substituted cycloalkyl having 4 to 8 carbon atoms, and an optionally substituted aryl, aralkyl or heteroaryl group selected from the group consisting of phenyl, benzyl, pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl;

where the optionally substituted alkyl and optionally substituted cycloalkyl can be substituted with 1 or 2 substituents independently selected from the group consisting of hydroxy, amino, N-alkylamino having 1 to 4 carbons, N,N-dialkylamino having a total of 2 to 6 carbons and alkoxy having 1 to 4 carbons; and where the optionally substituted aryl, aralkyl and heteroaryl groups are optionally substituted with 1 or 2 substituents independently selected from the group consisting of alkyl having 1 to 4 carbons, fluoro, chloro, bromo, acetyl, amino, nitro, cyano, trifluoromethyl, N-alkylamino having 1 to 4 carbons, N,N-dialkylamino having a total of 2 to 6 carbons, carboxyl, carboalkoxy having 1 to 4 carbons, carboxamido, sulfonamido, hydroxyalkyl having 1 to 4 carbons, aminoalkyl having 1 to 4 carbons, N-alkylaminoalkyl having 1 to 4 carbons in each of the alkyl portions, and N,N-dialkylaminoalkyl having a total of 2 to 6 carbons in the dialkylamino portion and 1 to 4 carbons in the alkyl portion;

$R^1$ is $X^3$;

$R^2$ is selected from the group consisting of optionally substituted alkyl having 1 to 6 carbons,

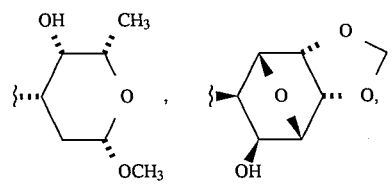

optionally substituted cycloalkyl having 3 to 8 carbons, and

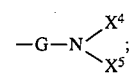

wherein the optionally substituted alkyl is optionally substituted with 1 or 2 substituents independently selected from the group consisting of hydroxy, cyano, amino, N-alkylamino having 1 to 4 carbons, N,N-dialkylamino having a total of 2 to 6 carbons, N-(hydroxyalkyl)amino having 2 to 4 carbons, N,N-bis(hydroxyalkyl)amino wherein each alkyl portion has 2 to 4 carbons, alkoxy having 1 to 4 carbons, alkoxycarbonyl having 1 to 4 carbons in the alkoxy portion, N,N-dialkylaminoalkoxy having a total of 2 to 6 carbons in the dialkylamino portion and 2 to 4 carbons in the alkoxy portion, alkoxyalkoxy having 1 to 4 carbons in each of the alkoxy portions, alkoxyalkoxyalkoxy having 1 to 4 carbons in each of the alkoxy portions,

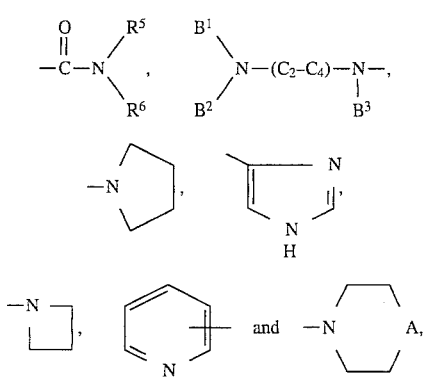

wherein $R^5$ and $R^6$ are independently selected from hydrogen or alkyl having 1 to 4 carbons, or $R^5$ and $R^6$ are taken together with the nitrogen to which they are attached and form a saturated or unsaturated ring having 4 to 6 carbon atoms, morpholino or piperazino;

A is $CH_2$, NH, O, S or N-loweralkyl; and $B^1$, $B^2$, and $B^3$ are each independently selected from the group consisting of hydrogen and $(C_1–C_4)$alkyl; the optionally substituted cycloalkyl is optionally substituted with 1 to 5 substituents independently selected from the group consisting of hydroxy, fluoro, chloro, alkoxy having 1 to 4 carbons, hydroxyalkyl having 1 to 4 carbons, alkoxyalkyl having 1 to 4 carbons in each of the alkoxy and alkyl portions, amino, N-alkylamino having 1 to 4 carbons, N,N-dialkylamino having a total of 2 to 6 carbons and

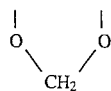

where the oxygen atoms are attached to adjacent carbon atoms of the cycloalkyl;

G is $(C_2–C_4)$alkylene optionally substituted with $(C_1–C_4)$alkyl or hydroxyl;

$X^4$ is selected from the group consisting of hydrogen, methyl and ethyl;

$X^3$ and $X^5$ are independently selected from the group consisting of an optionally substituted hydroxyalkanoyl having 1 to 6 carbons, an amino acyl group, and dipeptidyl group, wherein the amino acyl group and the amino acyl groups of the dipeptidyl group are independently selected from the group consisting of the D- or L-form, when applicable, of alanyl, arginyl, asparagyl, aspartyl acid, cysteinyl, cystyl, glutamyl acid, glutamyl, glycyl, histidyl, hydroxyllysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α, γ-diaminobutyryl, ornithyl, homoseryl, bicyl, N-N-diethyl-β-alanyl, N,N-dimethyl-γ-aminobutyryl and sarcosyl; and the optionally substituted hydroxyalkanoyl group is optionally substituted with an optionally substituted phenyl, wherein the optionally substituted phenyl is optionally substituted with 1 to 5 substituents selected from the group consisting of $(C_1–C_4)$alkyl, fluoro, chloro, bromo, iodo, $(C_1–C_4)$alkoxy, nitro, amino, cyano, hydroxy, trifluoromethyl and carboalkoxy having 1 to 4 carbons;

or $X^4$ and $X^5$ are taken together with the nitrogen to which they are attached and form

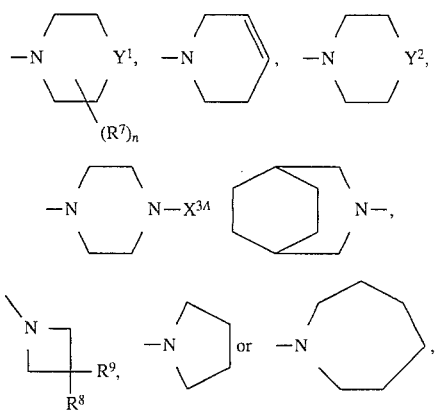

where $Y^1$ is selected from the group consisting of C, CH, $CH_2$, N and NH; $Y^2$ is O or S; n is 0, 1 or 2;

$R^7$ is alkyl having 1 to 4 carbons

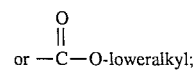

$R^8$ is H or alkyl having 1 to 4 carbons;

$R^9$ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or $R^8$ and $R^9$ are taken together and form an oxo group; and $X^{3A}$ is independently selected from the same group as $X^3$;

provided that:

(1) when $R^2$ is a substituted cycloalkyl, then the hydroxy and amino substituents cannot be attached to the 1-position of said substituted cycloalkyl; and (2) when $R^2$ is a substituted cyclopropyl or substituted cyclobutyl, then

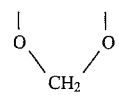

cannot be a substituent.

4. A compound of formula I

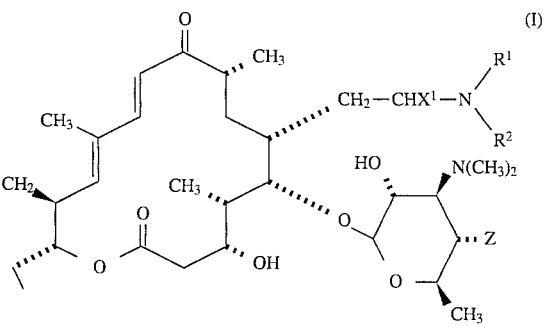

or a pharmaceutically acceptable salt thereof wherein $X^1$ is H or CN;

Z is H or OH;

Q is selected from the group consisting of H, OH, fluoro, chloro, bromo, iodo, $OX^2$, $SX^2$,

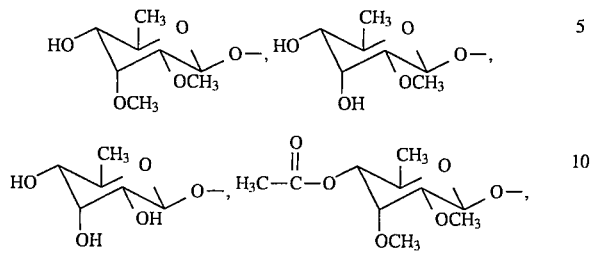

azetidin-1-yl, pyrrolidin-1-yl, piperidin-1-yl, 3,3-dimethylpiperidin-1-yl, hexahydroazepin-1-yl, octahydroazocin-1-yl, octahydroindol-1-yl, 1,3,3a,4,7,7a-hexahydroisoindol-2-yl, decahydroquinol-1-yl, decahydroisoquinol-2-yl, 1,2,3,4-tetrahydroisoquinol-2-yl, 1,2,3,6-tetrahydropyridin-1-yl, 4-alkylpiperazin-1-yl having 1 to 4 carbons in the alkyl portion, morpholino, 2,6-dimethylmorpholin-4-yl, thiomorpholino, and

where $R^3$ and $R^4$ are independently selected from the group consisting of H, alkyl having 1 to 4 carbons, hydroxyalkyl having 2 to 4 carbons, cycloalkyl having 3 to 8 carbons, alkenyl having 3 or 4 carbons, alkoxyalkyl having 1 to 4 carbons in the alkoxy portion and 2 to 4 carbons in the alkyl portion and alkoxyalkoxyalkyl having 1 to 4 carbons in each of the alkoxy portions and 2 to 4 carbons in the alkyl portion; and $X^2$ is selected from the group consisting of optionally substituted alkyl having 1 to 4 carbons, optionally substituted cycloalkyl having 4 to 8 carbon atoms, and an optionally substituted aryl, aralkyl or heteroaryl group selected from the group consisting of phenyl, benzyl, pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl;

where the optionally substituted alkyl and optionally substituted cycloalkyl can be substituted with 1 or 2 substituents independently selected from the group consisting of hydroxy, amino, N-alkylamino having 1 to 4 carbons, N,N-dialkylamino having a total of 2 to 6 carbons and alkoxy having 1 to 4 carbons; and where the optionally substituted aryl, aralkyl and heteroaryl groups are optionally substituted with 1 or 2 substituents independently selected from the group consisting of alkyl having 1 to 4 carbons, fluoro, chloro, bromo, acetyl, amino, nitro, cyano, trifluoromethyl, N-alkylamino having 1 to 4 carbons, N,N-dialkylamino having a total of 2 to 6 carbons, carboxyl, carboalkoxy having 1 to 4 carbons, carboxamido, sulfonamido, hydroxyalkyl having 1 to 4 carbons, aminoalkyl having 1 to 4 carbons, N-alkylaminoalkyl having 1 to 4 carbons in each of the alkyl portions, and N,N-dialkylaminoalkyl having a total of 2 to 6 carbons in the dialkylamino portion and 1 to 4 carbons in the alkyl portion;

$R^1$ is hydrogen or methyl;

$R^2$ is

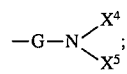

G is $(C_2-C_4)$alkylene optionally substituted with $(C_1-C_4)$alkyl or hydroxyl;

$X^4$ is selected from the group consisting of hydrogen, methyl and ethyl;

$X^5$ is selected from the group consisting of an optionally substituted hydroxyalkanoyl having 1 to 6 carbons, an amino acyl group, and dipeptidyl group, wherein the amino acyl group and the amino acyl groups of the dipeptidyl group are independently selected from the group consisting of the D- or L-form, when applicable, of alanyl, arginyl, asparagyl, aspartyl acid, cysteinyl, cystyl, glutamyl acid, glutamyl, glycyl, histidyl, hydroxyllysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α, γ-diaminobutyryl, ornithyl, homoseryl, N-N-diethyl-β-alanyl, N,N-dimethyl-γ-aminobutyryl and sarcosyl; and the optionally substituted hydroxyalkanoyl group is optionally substituted with an optionally substituted phenyl, wherein the optionally substituted phenyl is optionally substituted with 1 to 5 substituents selected from the group consisting of $(C_1-C_4)$alkyl, fluoro, chloro, bromo, iodo, $(C_1-C_4)$alkoxy, nitro, amino, cyano, hydroxy, trifluoromethyl and carboalkoxy having 1 to 4 carbons;

or $X^4$ and $X^5$ are taken together with the nitrogen to which they are attached and form

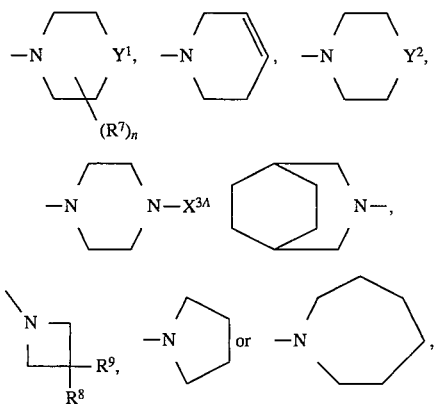

where $Y^1$ is selected from the group consisting of C, CH, $CH_2$, N and NH;

$Y^2$ is O or S; n is 0, 1 or 2;

$R^7$ is alkyl having 1 to 4 carbons

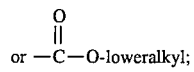

$R^8$ is H or alkyl having 1 to 4 carbons;

$R^9$ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or $R^8$ and $R^9$ are taken together and form an oxo group; and $X^{3A}$ is independently selected from the same group as $X^3$.

5. A compound of formula I

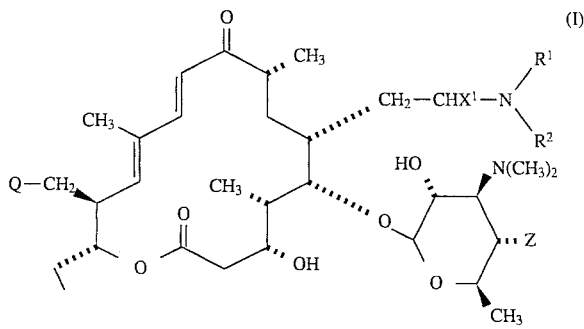

or a pharmaceutically acceptable salt thereof,
wherein Q is H;
Z is H;
$X^1$ is H;
$R^1$ is $X^3$ and
$R^2$ is methyl;
  where $X^3$ is selected from the group consisting of an optionally substituted hydroxyalkanoyl having 1 to 6 carbons, an amino acyl group, and dipeptidyl group, wherein the amino acyl group and the amino acyl groups of the dipeptidyl group are independently selected from the group consisting of the D- or L-form, when applicable, of alanyl, arginyl, asparagyl, aspartyl acid, cysteinyl, cystyl, glutamyl acid, glutamyl, glycyl, histidyl, hydroxyllysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α, γ-diaminobutyryl, ornithyl, homoseryl, bicyl, N-N-diethyl-β-alanyl, N,N-dimethyl-γ-aminobutyryl and sarcosyl; and
  the optionally substituted hydroxyalkanoyl group is optionally substituted with an optionally substituted phenyl, wherein the optionally substituted phenyl is optionally substituted with 1 to 5 substituents selected from the group consisting of $(C_1-C_4)$alkyl, fluoro, chloro, bromo, iodo, $(C_1-C_4)$alkoxy, nitro, amino, cyano, hydroxy, trifluoromethyl and carboalkoxy having 1 to 4 carbons.

6. A compound according to claim 2, or a pharmaceutically acceptable salt thereof, wherein $X^1$ is H; Z is H; $R^1$ is methyl and $R^2$ is 3-(dimethylamino)propyl.

7. A compound according to claim 3, or a pharmaceutically acceptable salt thereof, wherein wherein $X^1$ is H and $R^2$ is 3-(dimethylamino)propyl.

8. A compound according to claim 7, or a pharmaceutically acceptable salt thereof, wherein $X^3$ is an aminoacyl group selected from the group consisting of L-alanyl, D-alanyl, glycyl, L-valyl, N,N-dimethylglycyl, N,N-dimethyl-γ-aminobutyryl, N,N-dimethyl-β-alanyl, sarcosyl, α,α-dimethylglycyl and α-aminobutyryl.

9. A compound according to claim 8, or a pharmaceutically acceptable salt thereof, wherein Q is H, Z is H and $X^3$ is glycyl.

10. A compound according to claim 8, or a pharmaceutically acceptable salt thereof, wherein Q is H, Z is H and $X^3$ is L-alanyl.

11. A compound according to claim 4, or a pharmaceutically acceptable salt thereof, wherein G is propylene or 2,2-dimethylpropylene and $X^4$ is hydrogen or methyl.

12. A compound according to claim 11, or a pharmaceutically acceptable salt thereof, wherein $X^5$ is an aminoacyl group selected from the group consisting of L-alanyl, D-alanyl, glycyl, L-valyl, N,N-dimethylglycyl, sarcosyl, α,α-dimethylglycyl and α-aminobutyryl.

13. A compound according to claim 12, or a pharmaceutically acceptable salt thereof, wherein Q is H; Z is H; $R^1$ is hydrogen; $X^4$ is hydrogen; G is 2,2-dimethylpropylene; and $X^5$ is L-alanyl.

14. A compound according to claim 12, or a pharmaceutically acceptable salt thereof, wherein Q is H; Z is H; $R^1$ is methyl; $X^4$ is methyl; G is propylene; and $X^5$ is glycyl.

15. A compound according to claim 12, or a pharmaceutically acceptable salt thereof, wherein Q is H; Z is H; $R^1$ is methyl; $X^4$ is methyl; G is propylene; and $X^5$ is L-alanyl.

16. A pharmaceutical composition comprising an effective amount of a compound of claim 1 and a pharmaceutically acceptable carrier or diluent.

17. A method of treating a bacterial infection in an animal in need thereof which comprises administering to said animal a bacterial treating amount of a compound of claim 1 or a pharmaceutically acceptable salt thereof.

18. A method of treating a mycoplasmic infection in an animal in need thereof which comprises administering to said animal a mycoplasmic treating amount of claim 1 or a pharmaceutically acceptable salt thereof.

19. A pharmaceutical composition comprising an effective amount of a compound of claim 2 and a pharmaceutically acceptable carrier or diluent.

20. A pharmaceutical composition comprising an effective amount of a compound of claim 3 and a pharmaceutically acceptable carrier or diluent.

21. A pharmaceutical composition comprising an effective amount of a compound of claim 4 and a pharmaceutically acceptable carrier or diluent.

22. A pharmaceutical composition comprising an effective amount of a compound of claim 5 and a pharmaceutically acceptable carrier or diluent.

23. A method of treating a bacterial infection in an animal in need thereof which comprises administering to said animal a bacterial treating amount of a compound of claim 2 or a pharmaceutically acceptable salt thereof.

24. A method of treating a bacterial infection in an animal in need thereof which comprises administering to said animal a bacterial treating amount of a compound of claim 3 or a pharmaceutically acceptable salt thereof.

25. A method of treating a bacterial infection in an animal in need thereof which comprises administering to said animal a bacterial treating amount of a compound of claim 4 or a pharmaceutically acceptable salt thereof.

26. A method of treating a bacterial infection in an animal in need thereof which comprises administering to said animal a bacterial treating amount of a compound of claim 5 or a pharmaceutically acceptable salt thereof.

27. A method of treating a mycoplasmic infection in an animal in need thereof which comprises administering to said animal a mycoplasmic treating amount of claim 2 or a pharmaceutically acceptable salt thereof.

28. A method of treating a mycoplasmic infection in an animal in need thereof which comprises administering to said animal a mycoplasmic treating amount of claim 3 or a pharmaceutically acceptable salt thereof.

29. A method of treating a mycoplasmic infection in an animal in need thereof which comprises administering to said animal a mycoplasmic treating amount of claim 4 or a pharmaceutically acceptable salt thereof.

30. A method of treating a mycoplasmic infection in an animal in need thereof which comprises administering to said animal a mycoplasmic treating amount of claim 5 or a pharmaceutically acceptable salt thereof.

* * * * *